US006198253B1

United States Patent
Kurle et al.

(10) Patent No.: US 6,198,253 B1
(45) Date of Patent: *Mar. 6, 2001

(54) SMART BATTERY WITH MAINTENANCE AND TESTING FUNCTIONS, COMMUNICATIONS, AND DISPLAY

(75) Inventors: Wayne D. Kurle, Winston, GA (US); Stephen B. Johnson, Clinton, WA (US); Rockland W. Nordness, Kirkland, WA (US); Stephen L. Firman, Woodinville, WA (US); Douglas M. Gustavson, Guilford, CT (US); Peter Y. Choi, Lynnwood, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/471,695

(22) Filed: Dec. 23, 1999

Related U.S. Application Data

(63) Continuation of application No. 09/237,193, filed on Jan. 26, 1999, now Pat. No. 6,072,299.
(60) Provisional application No. 60/072,485, filed on Jan. 26, 1998.

(51) Int. Cl.$^7$ .......................... H01M 10/44; H01M 10/46
(52) U.S. Cl. ............................................................ 320/132
(58) Field of Search .................................. 320/127, 132, 320/134, 136, 149, FOR 142, FOR 147, DIG. 18, DIG. 21

(56) References Cited

U.S. PATENT DOCUMENTS

| 4,800,336 | 1/1989 | Mikami et al. |
| 4,885,523 | 12/1989 | Koenck |

(List continued on next page.)

FOREIGN PATENT DOCUMENTS

| 0 743 531A2 | 11/1996 | (EP) |
| 0 743 532A2 | 11/1996 | (EP) |
| 0 743 533A2 | 11/1996 | (EP) |

OTHER PUBLICATIONS

"System Management Bus Specification," *Smart Battery System Specifications,* Revision 1.0, Feb. 15, 1995. Benchmarq Microelectronics, Inc. et al., 1996.

(List continued on next page.)

*Primary Examiner*—Edward H. Tso
(74) *Attorney, Agent, or Firm*—Christensen O'Connor Johnson Kindness PLLC

(57) ABSTRACT

A smart battery that self-monitors and maintains information about itself that includes its state of charge, its need for maintenance, and for conditions that indicate that it has reached the end of its useful life and should be discarded. The information maintained by the battery is then either displayed on an on-board display or is communicated to another device on a communication bus. The state of charge quantifies the smart battery's ability to reliably deliver charge to a host device and is dynamically adjusted over the lifetime of the smart battery. The state of charge may not exceed a full charge capacity value maintained by the smart battery and initially set to an estimated value. This full charge capacity value is dynamically adjusted throughout the life of the smart battery using information accumulated and maintained by the smart battery that indicates the smart battery's actual performance during use and by using messages received from a battery maintenance and testing system. The smart battery also accumulates and maintains information that indicates that the smart battery requires maintenance. A battery maintenance and testing system can read this need for maintenance from the smart battery and take the steps necessary to automatically maintain the smart battery. Conditions that indicate that the battery is defective or has exceeded its useful life are also maintained by the smart battery and communicated through the on-board display or to another devices over a communication bus. The battery is specially configured for easy assembly.

47 Claims, 14 Drawing Sheets

U.S. PATENT DOCUMENTS

| | | |
|---|---|---|
| 5,130,659 | 7/1992 | Sloan . |
| 5,455,499 | 10/1995 | Uskali et al. . |
| 5,578,915 * | 11/1996 | Crouch, Jr. et al. . |
| 5,606,242 * | 2/1997 | Hull et al. . |
| 5,625,291 | 4/1997 | Brink et al. . |
| 5,721,482 | 2/1998 | Benvegar et al. . |

OTHER PUBLICATIONS

"System Management Bus Specification," *Smart Battery System Specifications,* Revision 1.0, Jun. 27, 1996. Benchmarq Microelectronics, Inc. et al., 1996.

Nass, Richard, "Specification Paves the Way for Intelligent Batteries," *Wireless Systems Design,* Nov. 1997, pp. 25–32.

* cited by examiner

SMART BATTERY WITH MAINTENANCE AND TESTING FUNCTIONS, COMMUNICATIONS, AND DISPLAY

RELATIONSHIP TO OTHER APPLICATIONS

This application is a continuation and claims the benefit of prior application Ser. No. 09/237,193, filed Jan. 26, 1999, now U.S. Pat. No. 6,072,299, which in turn claims the benefit of U.S. Provisional Application Serial No. 60/072,485 filed Jan, 26, 1998. The disclosure and drawings of application Ser. No. 09/237,193 and Provisional Application Serial No. 60/072,485 are specifically incorporated herein by reference.

FIELD OF THE INVENTION

The present invention relates generally to the field of rechargeable batteries, and more particularly to an intelligent battery that internally monitors its own operating condition, its own need for maintenance, and its own useful life, and communicates this information to a user or to an intelligent device.

BACKGROUND OF THE INVENTION

With the proliferation of portable electronic devices, the use of rechargeable batteries has become increasingly important. Rechargeable batteries can now be found in devices as simple as a flashlight, as important as notebook computers, and as vital as portable medical equipment. An example of a portable medical device which is dependent on a rechargeable battery pack is a portable defibrillator unit.

Portable defibrillator units are used by emergency medical technicians on persons suffering from certain types of abnormal heart rhythms, e.g., ventricular fibrillation, to shock the heart back into a normal beating pattern. Although many of these portable defibrillators have the ability to operate off of AC line current, when used in the field, portable defibrillators are almost totally dependent on rechargeable battery packs. The portable battery packs provide the power both to operate the internal electronics of the defibrillator and to provide the charge source for the therapeutic shock. In order to provide the power source for charging the shock delivery circuitry of the defibrillator, it is necessary that the portable battery pack be capable of providing a relatively large current draw over a relatively short period of time. If the battery is unable to supply this current when demanded, the delivery of the therapeutic shock may be delayed or prohibited.

Seconds count in the application of the therapeutic shock to a person suffering a heart attack. Swapping a bad battery pack in and out of a defibrillator may waste this precious time, as may waiting for a marginally functional battery to deliver the charge necessary for the therapeutic shock. It is important, therefore, for the user of a portable defibrillator to make sure that a reliable, working battery pack is available. This has usually meant having an ample supply of extra battery packs on hand. Unfortunately, one can usually only guess the battery pack's ability to reliably deliver high current charging pulses. While users normally log the age and use of the battery manually to predict its current condition, the accuracy of the predictions are both dependent on the accuracy of the records and the validity of the underlying assumptions of the predictions.

In response to the demand for reliable batteries, computer and battery manufacturers have recently been developing "smart batteries" which internally measure battery variables such as voltage and current flow in and out of the battery and then apply predictive algorithms to estimate the battery's state of charge. The battery's predicted state of charge can then be communicated to a portable electronic device such as a notebook computer (i.e., a "host") over a communication bus. This is useful in applications where a computer needs to find out if there is enough charge in the battery to save a word-processing file to a disk drive. However, the prediction of a smart battery's state of charge must be much more reliable in medical device equipment, such as a defibrillator, where the state of charge is crucial to the appropriate medical treatment of an individual. This is particularly true if the only way to determine if the battery is able to deliver the charge is by first inserting it into the host unit.

The basic method for keeping track of the state of charge ("SOC") of a smart battery is to create a coulomb counter that adds the electrons going in and subtracts the electrons going out from a running counter. However, energy that goes into the battery does not all end up as stored charge—some of it is expended as heat in the charging process. For this reason an 'Efficiency Coefficient' (EC) is used to maintain the accounting. An EC can be estimated based on testing a statistically significant sample of batteries and choosing a value that represents the worst case battery. One method devised by the industry to avoid the error in calculating SOC is to establish a value for a fully charged battery and then cease accounting for the charge once the calculated charge has reached this value, regardless of measured input current.

The ability of a battery to deliver its charge on demand depends both on battery charge and proper battery maintenance. Rechargeable battery packs are currently manufactured using a number of known battery chemistries, including nickel cadmium (NiCd), sealed lead acid (SLA), nickel-metal hydride (NiMH), lithium ion (Li-ion), lithium polymer (Li-polymer), and rechargeable alkaline. The most popular choice for rechargeable batteries is currently the NiCd chemistry because it is relatively inexpensive, is fast and easy to charge, has excellent load performance even at cold temperatures, and is capable of withstanding a high number of charge/discharge cycles. Over the course of the life of the NiCd battery, however, the cycling of the battery causes it to develop crystalline formations that substantially decreases the battery's ability to hold charge. This is commonly referred to as "memory". It is known that "conditioning" the battery, which involves fully discharging the battery and then charging the battery back to the state of full charge, can substantially reduce NiCd memory. This process helps breakdown the crystalline structure developed over time and enables the battery to receive and store a greater charge.

If the NiCd "memory" goes undetected, the battery may show a voltage that indicates a full charge while it actually does not hold sufficient charge to supply the high current pulse required by a demanding application such as a portable defibrillator. While this "memory" problem has long been recognized, the conditioning required to correct it has depended on the user manually conditioning the battery on a regular basis. This meant that the user had to estimate when the battery required conditioning and then manually put the battery through a conditioning process. The actual discharging and charging of the battery during conditioning can take hours during which the battery is out of service. Due to these limitations, rechargeable battery packs are sometimes used past the period in which they should be conditioned, used until they fail, or are simply discarded much earlier than they would actually need to be if they were properly maintained.

Accordingly, a method and apparatus for a rechargeable battery pack that informs the user that the battery pack is ready to use, requires maintenance, or should be discarded, is needed. Further, the method and apparatus should be able to communicate with an intelligent battery maintenance and testing system that can charge, condition, and test the battery in accordance with the information that the battery maintains. As explained in the following, the present invention provides a method and apparatus that meets these criteria and solves other problems in the prior art.

SUMMARY OF THE INVENTION

In accordance with the present invention, an intelligent battery is provided which is capable of self-monitoring its state of charge, its need for maintenance, and the end of its useful life. The battery includes a user interface and display through which information regarding the state of charge, maintenance requirements and end of useful life can be displayed to a user or requested by a user by pushing a depressible keypad. In addition, the battery includes a monitoring circuit for self-monitoring that includes a communication interface for communicating this information to another device.

In one embodiment of the present invention, the monitoring circuit of the intelligent battery comprises an internal circuit board connected by a plurality of conductive rods to a plurality of external communication interface pads and a plurality of external voltage terminals located along a longitudinal axis that is near an edge of a bottom surface of the battery, such that the external communication interface pads are located between the external voltage terminals. The external communication interface pads electrically couple the battery to another device so that the battery may communicate with the other device. Further, the circuit board, conductive rods and external communication interface pads are positioned such that a lighted display and a momentary contact switch disposed on the upper surface of the circuit board are aligned directly beneath the user interface and display and the depressible keypad, respectively, disposed on a top surface of the battery. This arrangement allows the conductive rods to ascend through the interior of the battery to secure the placement of the circuit board beneath the user interface and display and electrically couple the circuit board to the external communication interface pads.

In accordance with other aspects of the invention, the circuit board of the battery includes a processing unit coupled to a non-volatile memory and a communication interface. The non-volatile memory stores the program code necessary for monitoring the battery, storing monitored information and communicating this information via the communication interface. More specifically, the information monitored and stored in the non-volatile memory includes: the full charge capacity of the battery; the time expired since the last successful battery condition; the total number of charge/discharge cycles; the number of charge/discharge cycles since the last condition; and the amount of time that the battery has operated in a temperature range that exceeds a recommended maximum temperature; a log of critical errors; and a set of flags indicating non-critical errors.

In accordance with yet other aspects of the present invention, the battery uses the monitored information to perform a plurality of tests for determining if the battery is in working condition, if the battery needs maintenance, or if the battery needs to be discarded. Once the tests are performed, the battery may communicate the results to another device, such as a battery maintenance and testing system, in order to receive the appropriate maintenance, or the results of the tests may be output on the lighted display and thus, communicated to the user.

In accordance with other aspects of the invention, the smart battery dynamically calculates its state of charge, which it stores in its memory as a state of charge value (SOC). The SOC is individually adjusted for each smart battery, throughout the life of that smart battery, by a method of the invention that compares the computed SOC (maintained by the smart battery) with an actual state of charge as determined by a battery maintenance and testing system When charged by the battery maintenance and testing system, the smart battery updates its state of charge value (SOC) until the battery maintenance and testing system determines that the smart battery is no longer accepting charge. When fully charged, the battery maintenance and testing system sends an End of Charge message to the smart battery which then sets its SOC to a full charge capacity value (FCC) that is also maintained in the smart battery's memory. During maintenance of the smart battery, the full charge capacity value (FCC) is adjusted by the smart battery when the battery maintenance and testing system sends an End of Discharge message to the smart battery to reflect any discrepancy between the SOC and the actual measurement of the state of charge made by the smart battery maintenance and testing system.

DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

Figure 1:
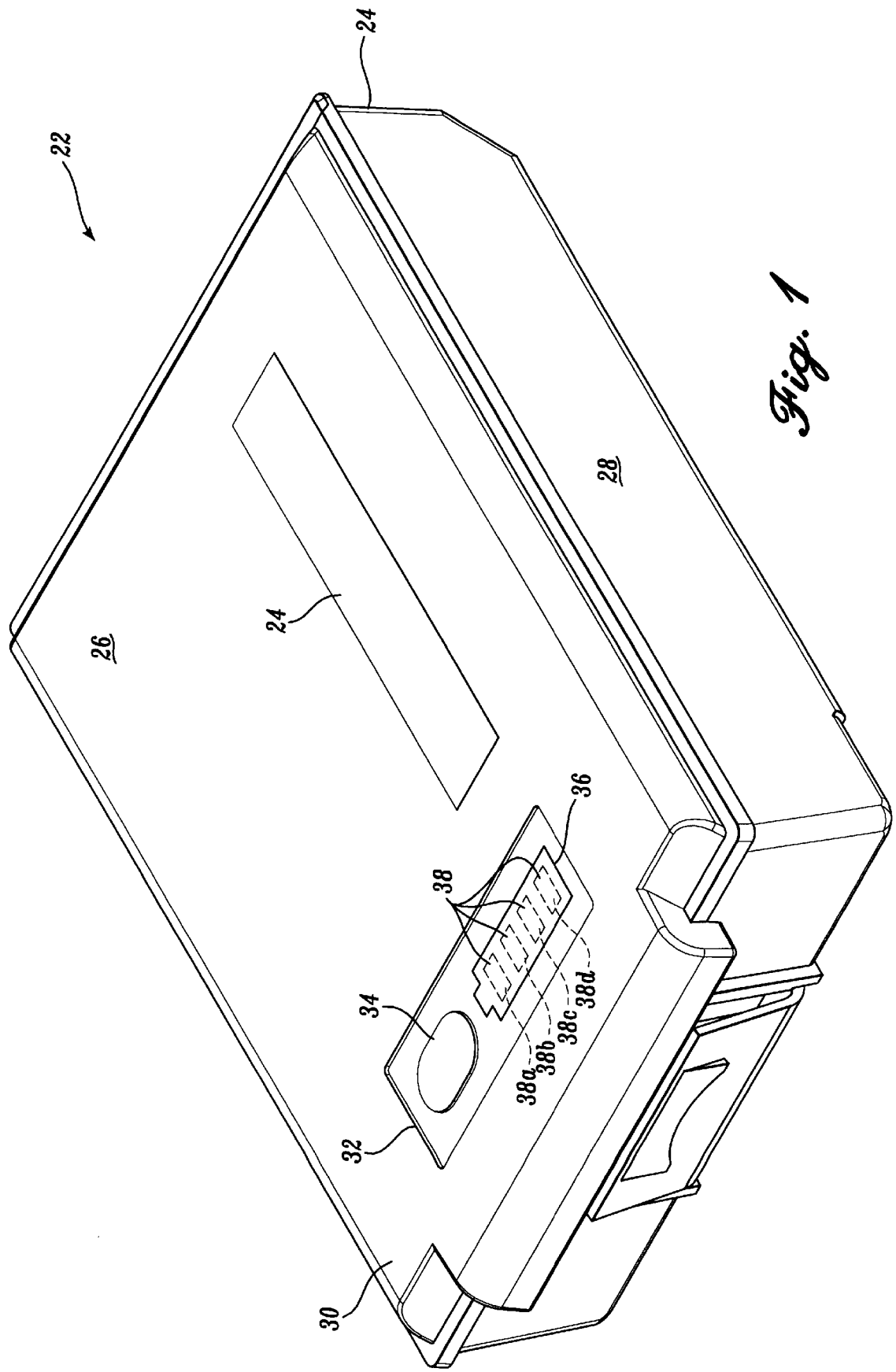
FIG. 1 is an elevated perspective view of an upper portion of a battery formed in accordance with a first embodiment of the present invention.

An "intelligent" or "smart" battery 22 formed in accordance with the present invention is shown in FIG. 1. The battery 22 has a housing 24 that is comprised of an upper portion 26 and a base portion 28. A user interface and display area 32 for displaying battery information to a user and for receiving requests from the user is disposed near a forward portion 30 of the upper portion 26. The user interface and display area 32 is comprised of a depressible keypad 34 and an opaque window section 36. Shown in phantom within the opaque window 36 are four channels 38 that segment the opaque window into four separate display zones 38a, 38b, 38c, 38d. The opaque window 36 is preferably shaped like a battery to indicate to the user that it displays the condition of the battery. The top cover 26 also has a display area 40 where product and manufacturer identification or instructions for the use of the smart battery can be placed.

Figure 2:
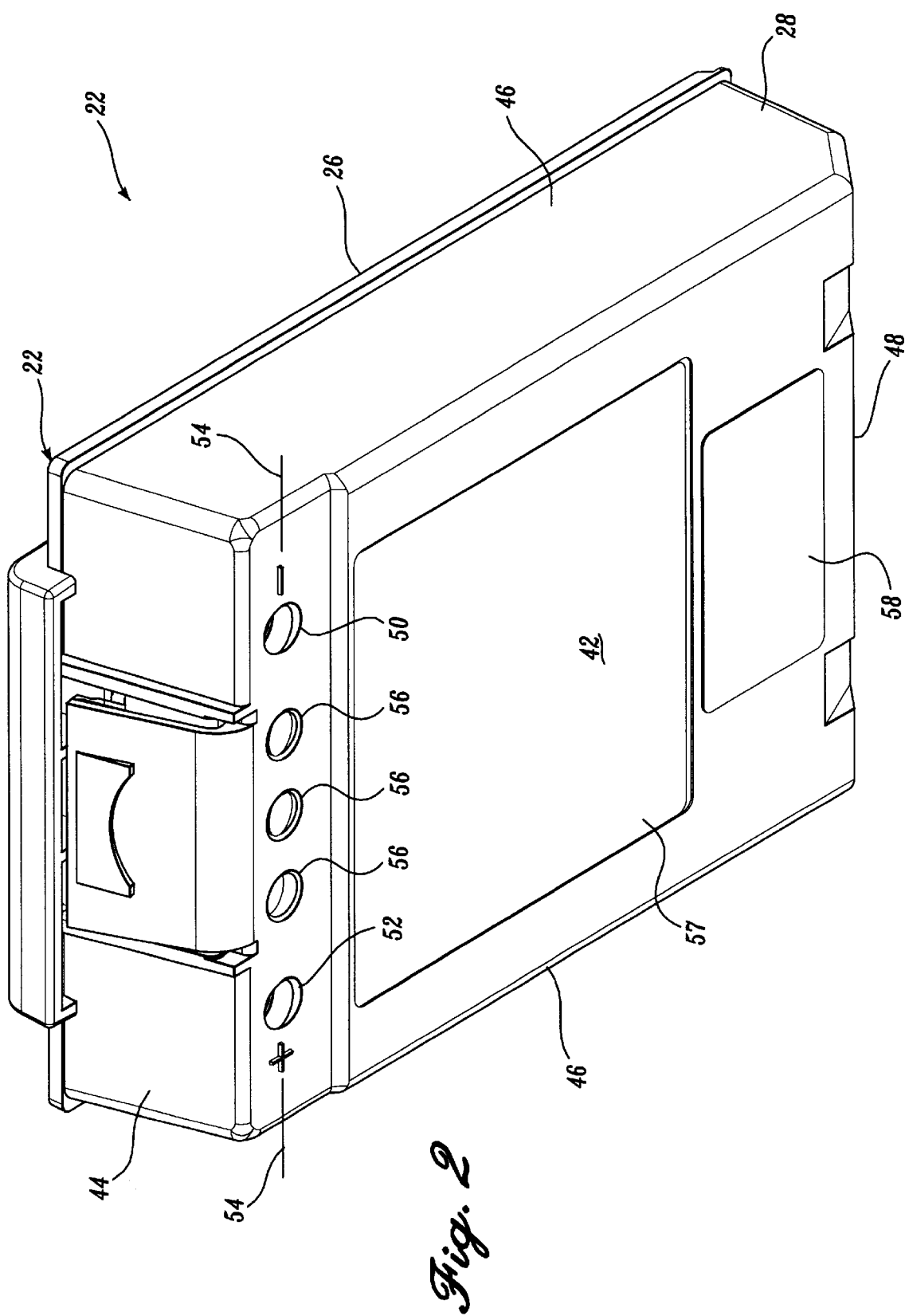
FIG. 2 is a perspective view of a bottom portion of the battery shown in FIG. 1.

A bottom view of the battery 22 is shown in FIG. 2. The base portion 28 has a bottom face 42, a first end 48, side faces 46 and a second end 44. A first voltage receptacle or aperture 50 and a second voltage receptacle or aperture 52 are located on the bottom face 42 near the bottom face's intersection with the second end 44. The first and second voltage receptacles 50 and 52 are aligned upon a longitudinal axis 54 in parallel with the intersection of the bottom face 42 and the second end 44. Also located on the bottom face 42 along the longitudinal axis 54 and between the first and second voltage receptacles 50 and 52 are three communication interface pads 56 (also referred to as circular conductive contacts), which electrically couple with another device, such as a battery maintenance and testing system, so that the battery 22 may communicate with the other device. Two indented display areas 57 and 58 are provided for the placement of identification, registration and instruction stickers.

Figure 3:
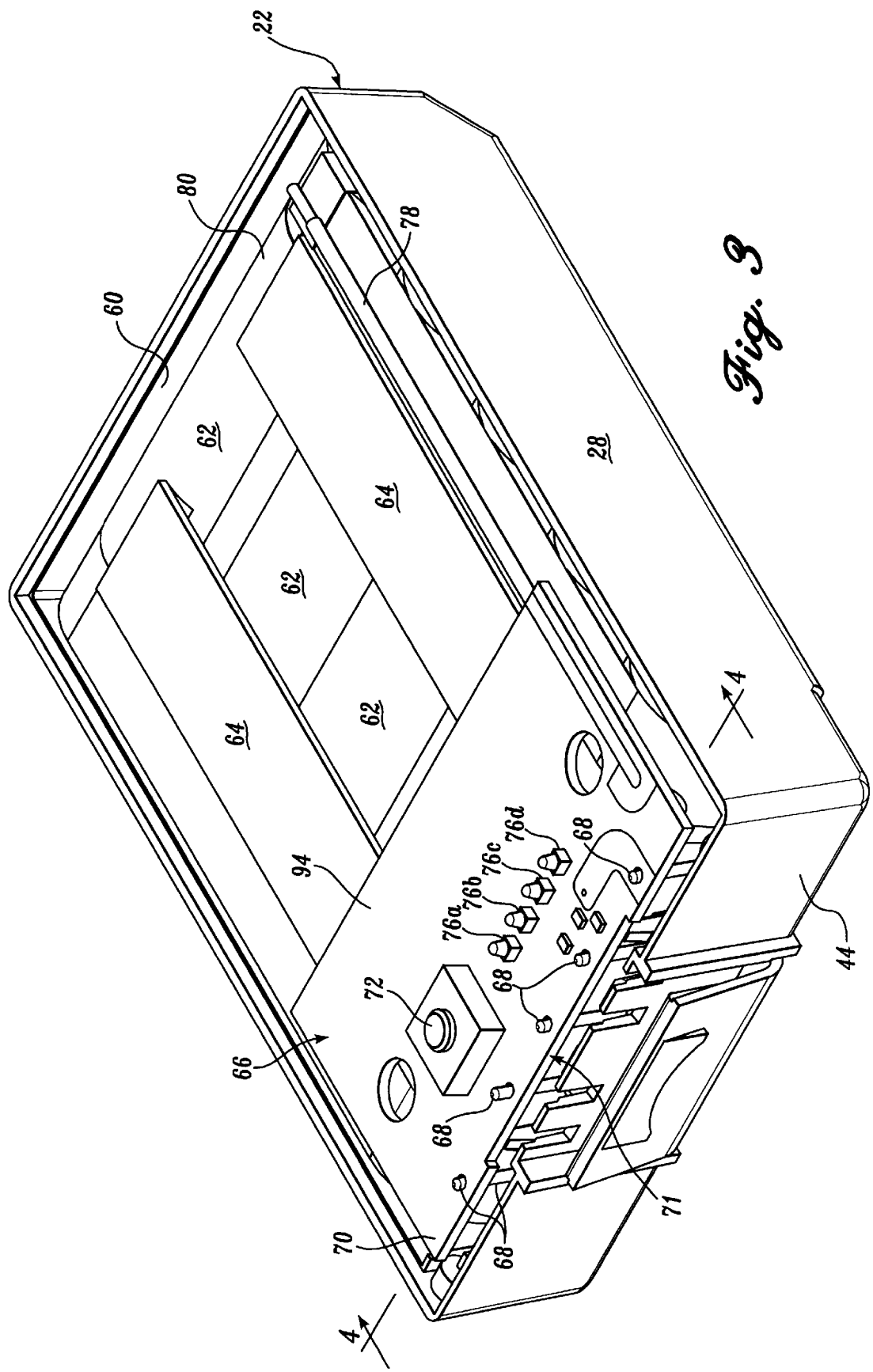
FIG. 3 is a perspective view of the battery shown in FIG. 1 with the upper portion removed and the contents of the battery exposed, including an internal circuit board.

In FIG. 3, the upper portion 26 of the battery 22 has been removed exposing a monitoring circuit 71 deposited in an interior portion 60 of the base portion 28 of the battery 22. The interior portion 60 also contains ten nickel cadmium battery cells connected in series and grouped together in five cell tubes 62. The battery cell tubes 62 are held in position by two pieces of foam core tape 64 on the top and two below (not shown) adhering the cells 62 to the base portion 28. The monitoring circuit 71 includes a circuit board 66, which rests above the battery cell tubes 62 upon the foam core tape, and five conductive rods 68 coupled to the circuit board 66 near its forward edge 70. A wire 78 electrically couples the negative terminal of a first battery cell with the circuit board 66. As will be described in more detail below, the conductive rods 68 secure the circuit board 66 directly below the user interface and display area 32 disposed on the top cover 26 of the battery 22 and directly above the communication interface pads 56.

Figure 4:
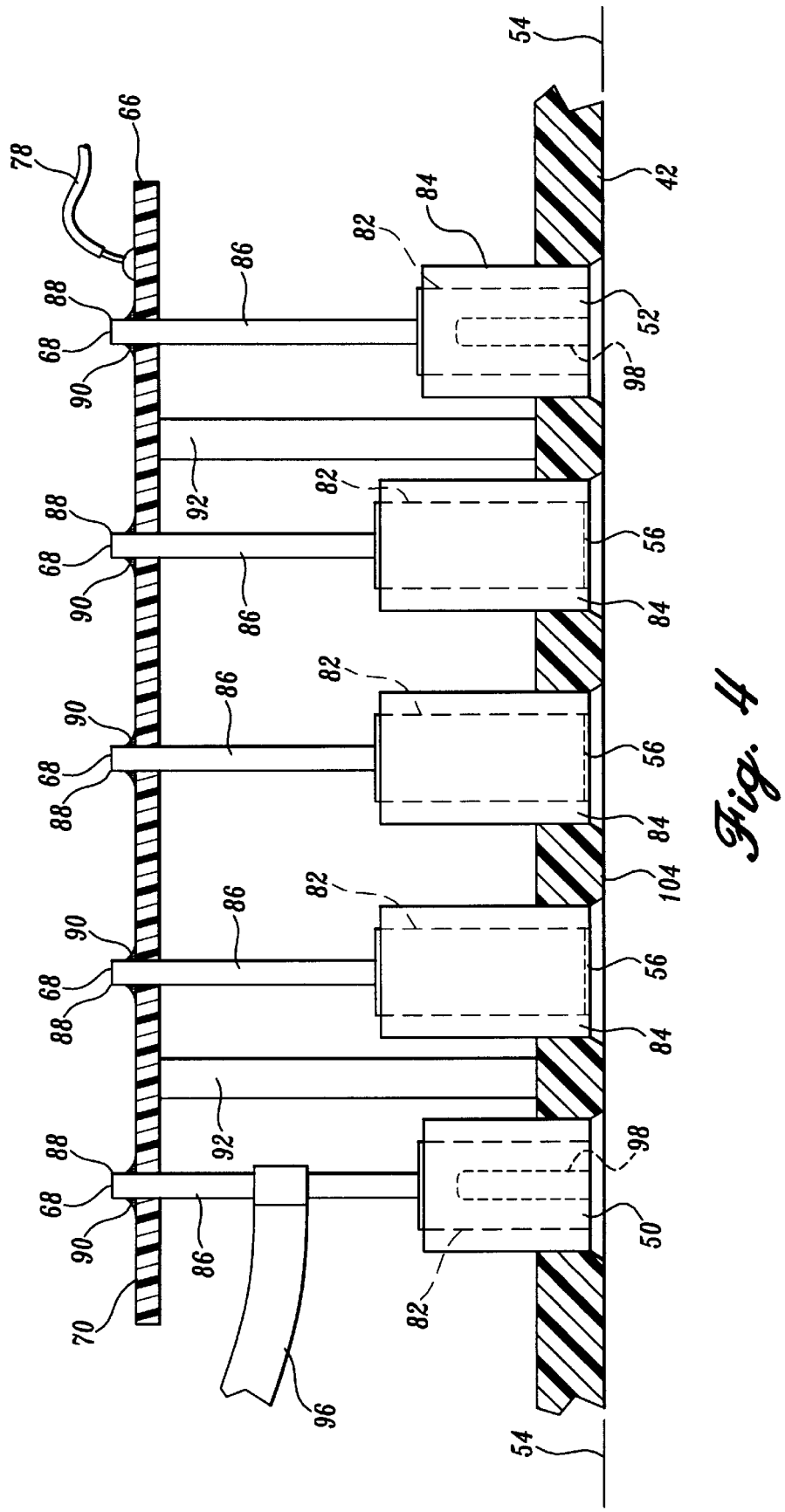
FIG. 4 is a partial, cross-sectional view of the battery shown in FIG. 3 taken along the line 4—4 and exposing a communication interface assembly formed in accordance with the present invention.

The electrical and mechanical effect of the connection of the circuit board 66 to the conductive rods 68, i.e., of the monitoring circuit 71, will now be discussed in more detail with reference to FIG. 4. FIG. 4 is a cross-sectional view of the battery 22 along line 44 of FIG. 3. It can be clearly seen from this view that the alignment of first voltage receptacle 50, the second voltage receptacle 52 and the three communication interface pads 56 along the longitudinal axis 54 advantageously allows the conductive rods 68 to serve as the structural support that holds the circuit board 66 in position directly below the user interface and display area 32 and directly above the communication interface pads 56. In this regard, a lower portion 82 of each conductive rod 68 is molded into a circular plastic well 84 that is part of the bottom face 42 of the base portion 28. Each conductive rod 68 also has a rigid intermediate portion 86 and a top portion 88 that is soldered to a conductive pad 90 on circuit board 66. During assembly, the circuit board 66 is soldered into position with the forward edge 70 of the circuit board 66 resting on support walls 92 that are part of the base portion 28 of the battery 22, and a rear end 94 of the circuit board resting upon the foam core tape 64 and battery cell tubes 62.

As noted above, each conductive rod 68 couples a communication interface pad 56 or a voltage receptacle 50 or 52 on the bottom face 42 of the battery 22 to the circuit board 66. The rigid intermediate portion 86 of the conductive rod 68 for the first voltage receptacle 50 is also coupled to the battery cells 62 by a soldered lead 96. The first voltage receptacle 50 and the second voltage receptacle 52 include a blind hole 98 for the reception of a banana plug from a defibrillator, a battery maintenance and testing system or some other device which passes current from or to the battery 22.

Each communication interface pad 56 may be electrically coupled with a host defibrillator, a host battery maintenance and testing system, or some other host device equipped with compatible communication interface hardware and software so that the communication interface pad may communicate certain signals to and from the host device. In an actual embodiment of the present invention described herein, one of the communication interface pads 56 communicates a CLOCK signal, another communicates a DATA signal, and the last communicates a THERMISTOR signal. Consequently, the respective conductive rods 68 electrically couple the CLOCK signal, DATA signal and THERMISTOR signal to the circuit board 66.

The circuit board 66 is positioned directly beneath the user interface and display area 32 when the upper portion 26 of the battery 22 is placed in position over the base portion 28. Consequently, when a user pushes the depressible keypad 34 of the user interface and display area 32, contact is made with a momentary contact switch 72 (FIG. 3), which is mounted on the upper surface 74 of the circuit board 66 and aligned below the depressible keypad 34 (FIG. 1). The circuit board 66 also includes a lighted display 76 consisting of four light emitting diodes (LED's) 76a–d, which is positioned on the upper surface 74 of the circuit board 66 so that the four LED's 76a–d align directly below the four corresponding channels 38a–d of the opaque window 36 disposed on the top cover 26 of the battery. Consequently, when the user pushes the depressible keypad 34, a state of charge of the battery is output on the LED's 76a–d of the display 76 and seen by the user through the corresponding channels 38a–d of the user interface and display area 32. As can be appreciated from the preceding description, the precise alignment of the circuit board 66 is important in order to position the momentary contact switch 72 below the depressible keypad 34 and the LED's of the lighted display 76 below their corresponding channels 38 in the opaque window 36.

Figure 5:
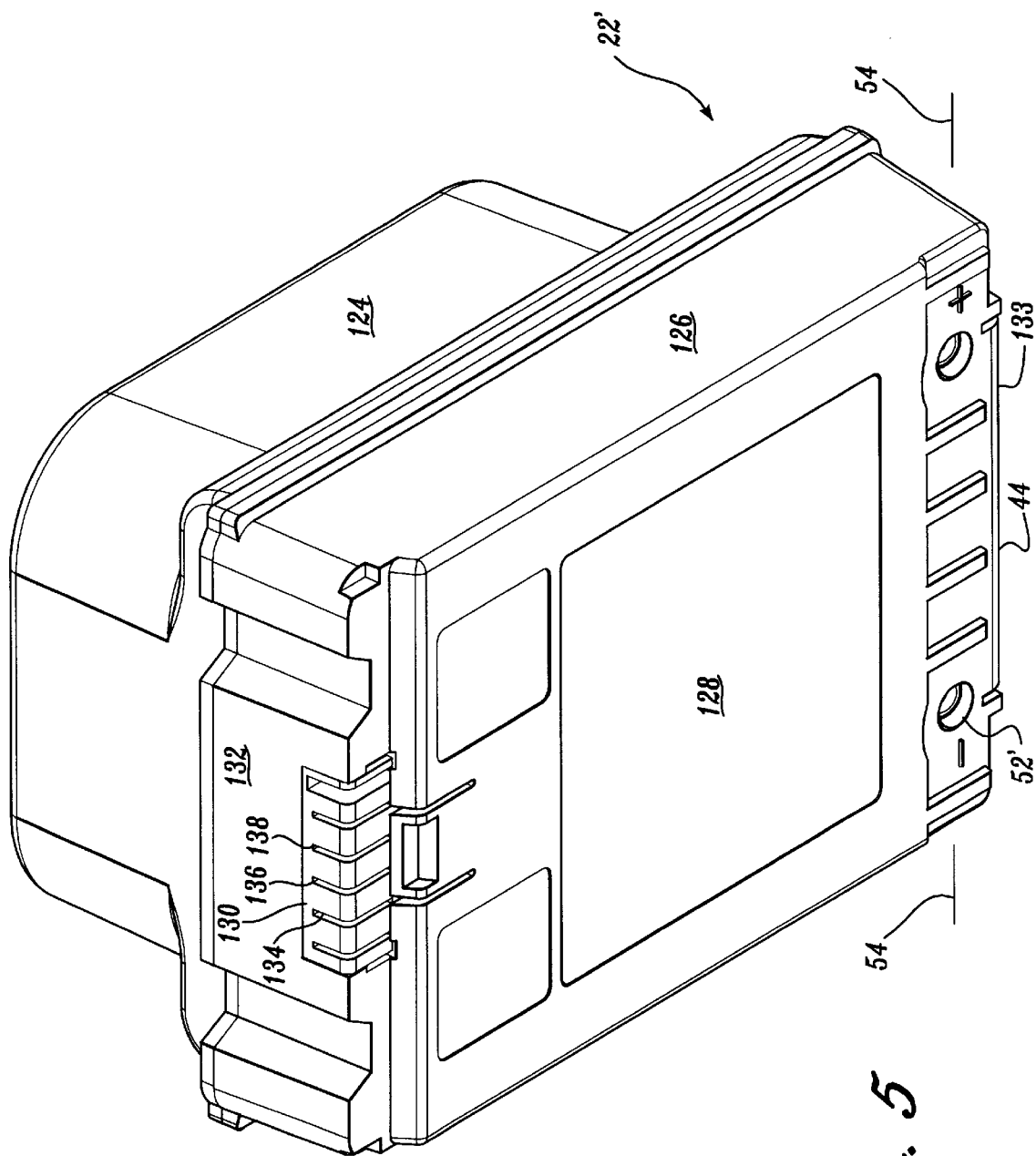
FIG. 5 is a perspective view of a bottom portion of a battery formed in accordance with a second embodiment of the present invention.

Another embodiment of a "smart" battery 22' is shown in FIG. 5. The battery 22' is essentially the same as the battery 22 shown in FIGS. 1–3 except that it does not include the user interface and display area 32 or the communication interface pads 56. Rather, the battery 22' substitutes a blade connector 130 at an opposite end of the battery 22' for the communication interface pads 56 used in the first embodiment of the smart battery 22. The battery 22' includes an upper portion 124 and a base portion 126 with a bottom face 128 and a first end 132. The shape of the upper portion 124 is configured to accommodate sealed lead acid (SLA) battery cells. The shape of the upper portion 124, however, is unimportant to the operation of the battery 22, or 22' and can be modified to accommodate any battery cell type or chemistry. It will further be appreciated that in other embodiments of the present invention, a user interface and display area 32 may be disposed on the upper portion 124 of the battery 22'.

A first voltage receptacle or aperture 50' and a second voltage receptacle or aperture 52' are aligned along a longitudinal axis 54' parallel to the intersection of a second end 133 and the bottom face 128. The blade connector 130 is provided at the intersection of a first end 132 and the bottom face 128. The blade connector 130 provides a path for coupling a CLOCK signal 134, a DATA signal 136, and a THERMISTOR signal 138 to an internal circuit board connected by a series of wires (not shown). It will be appreciated that the internal circuit board employed by the second embodiment of the battery 22' is essentially the same as the circuit board 66 employed by the first embodiment of the battery 22.

Figure 6:
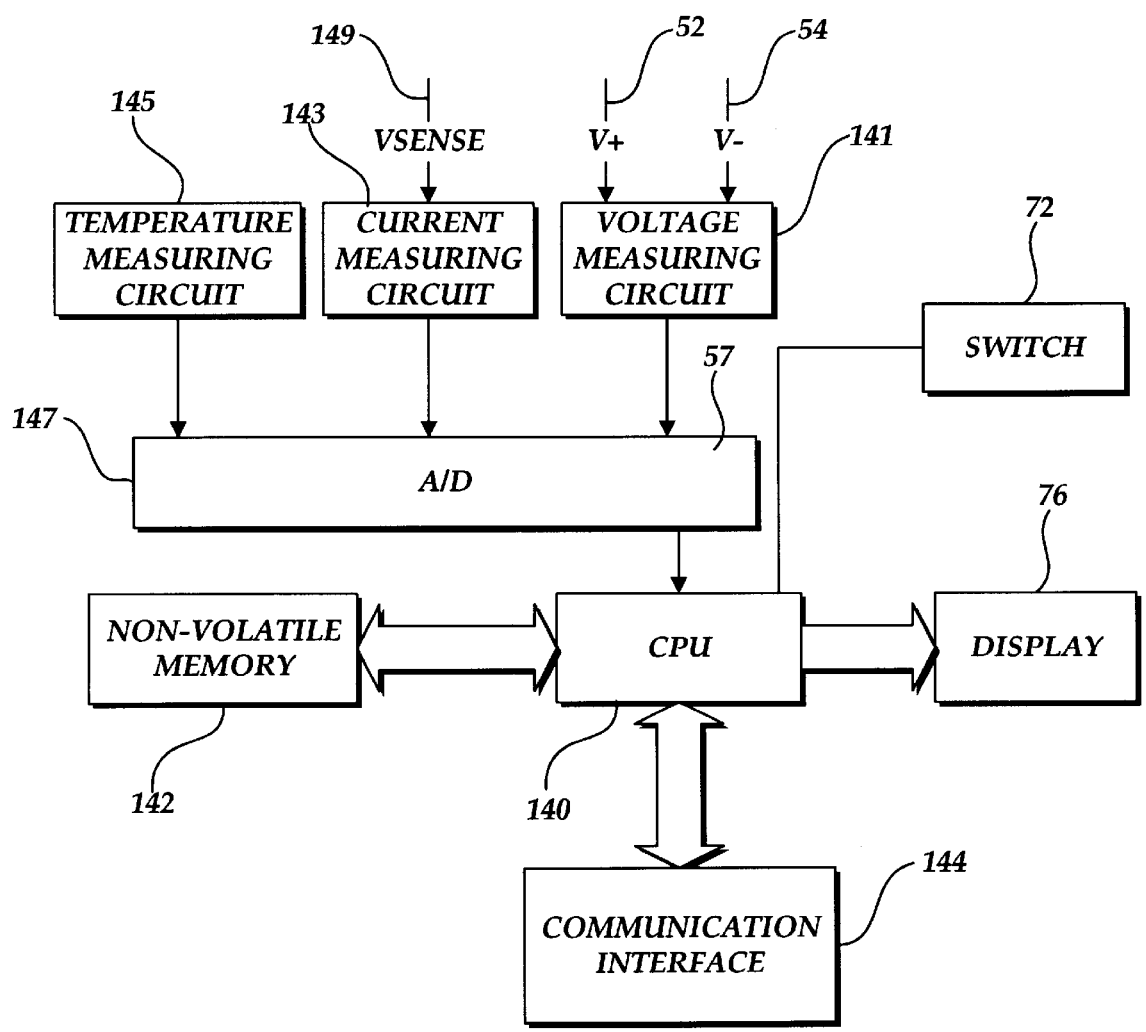
FIG. 6 is a block diagram of the internal circuit board shown in FIG. 3.

The components that comprise the monitoring circuit 71 are shown in block form in FIG. 6. The monitoring circuit 71 includes a central processing unit ("CPU") 140 that is coupled to the momentary contact switch 72, the lighted display 76, a non-volatile memory 142 and a communication interface 144. The communication interface 144 is used to communicate information between the battery 22 and a host defibrillator, battery maintenance and testing system or other device. In the actual embodiment of the present invention described herein, the communication interface 144 communicates with external devices in accordance with a bidirectional communication bus standard known as SMBus. The SMBus standard is more specifically described in the *System Management Bus Specification* (Revision 1.0 Feb. 15, 1995) developed by a consortium of battery and computer manufacturers and incorporated herein by reference. The SMBus standard uses an $I^2C$ bus as its backbone, which is discussed in detail in the document entitled *The $I^2C$ Bus and How to Use it* by Philips Semiconductors and incorporated by reference herein. The actual communication between the battery 22 and other devices is discussed in detail in commonly owned U.S. patent application Ser. No. 09/013,409, entitled BATTERY MAINTENANCE AND TESTING SYSTEM filed concurrently herewith, the disclosure and drawings of which are incorporated herein by reference.

The battery 22 monitors its voltage by using a voltage measuring circuit 141, a current measuring circuit 143 and temperature measuring circuit 145 that are all connected to an analog-to-digital ("A/D") converter 147 that is coupled to the CPU 140. The current measuring circuit 143 computes the current flowing through a reference resistor which is proportional to the voltage across the Vsense resistor 149. The temperature measuring circuit 145 employs a thermistor and the voltage measuring circuit 141 is measured across the battery cell voltage terminals 50 and 52.

Figure 7A:
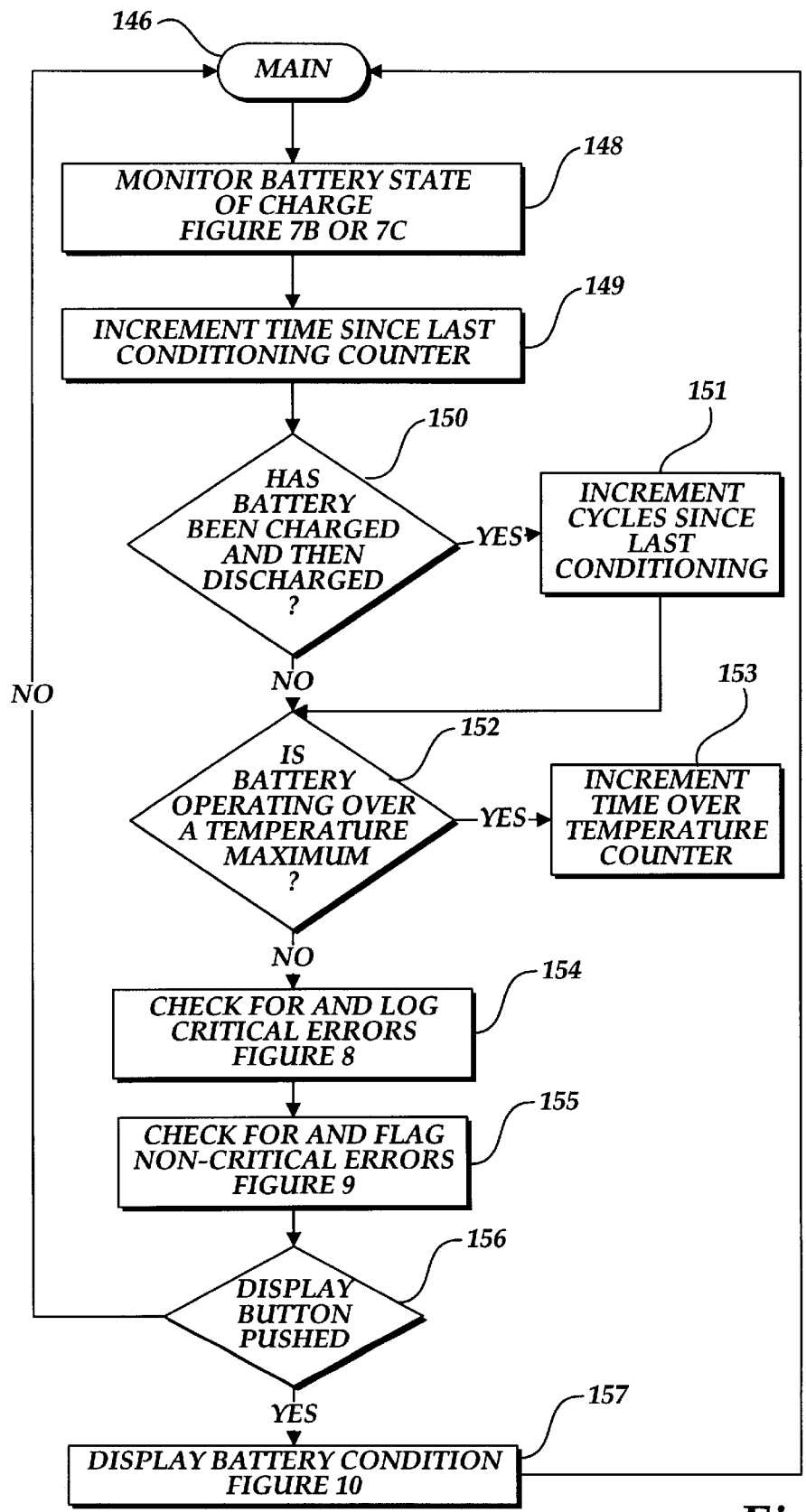
FIG. 7A is a flow chart illustrating the logic used by the battery of the present invention to monitor and test itself.

Now that the components of the monitoring circuit 71 have been described, the program code stored in the non-volatile memory 142 and executed by the central processing unit 140 will be discussed in more detail. In this regard, FIG. 7A illustrates the main processing routine 146 used by the central processing unit 140 to monitor and test the battery 22. The logic begins in a block 146 and then proceeds to a block 148 where it determines the batterys state of charge. The logic employed by the battery 22 to monitor its state of charge will be described in more detail below in connection with FIGS. 7B and 7C. It then increments, in a block 149, a counter which keeps track of the time since the smart battery 22 was last conditioned. In a decision block 150, the logic determines if the battery 22 has been cycled (charged and discharged). If so, the cycle counter is incremented in a block 151. If the result of decision block 150 is negative, the logic proceeds to a decision block 152 where it determines if the battery is operating at a temperature that is above a predefined maximum temperature. If so, a time over temperature counter is incremented in a block 153. Otherwise, the logic proceeds to a block 154 where it checks for and logs critical errors that would indicate the battery needs to be discarded. The logic used by the smart battery to check for and log critical errors is discussed in more detail below in reference to FIG. 8. The battery then checks for and flags non-critical errors indicating the need for maintenance in a block 155, which will be described in more detail below in reference to FIG. 9. If at any time the user pushes the depressible keypad 72 or if the battery was removed from the battery maintenance and testing system, this is detected in a decision block 156 and the battery displays its condition in a block 157 by lighting the appropriate LED's 76a–d of the lighted display 76 in predefined patterns that indicate the status of the smart battery 22. If the depressible keypad has not been pushed, or if it has been pushed and the battery condition displayed, the main logic depicted in FIG. 7A is repeated.

The present invention also improves upon the accuracy of keeping track of the battery's state of charge (SOC). It has been found that the efficiency coefficient (EC) is different depending upon the state of charge of the battery—higher at the beginning of the charge cycle, lower at the end. Additionally, variations within the process of constructing the battery influence the EC such that there is a distribution of EC values even within a single manufacturer's product. Therefore, applying a constant EC for all batteries of a certain type as is done in the simple EC method found in the background art for calculating SOC is susceptible to inaccuracies caused by actual variations in the EC that occur during the charge cycle; inaccuracies caused by variations in battery construction; and inaccuracies caused by conservatively choosing a worst case value as an EC. It also should be appreciated that inaccuracies that are introduced into the running SOC total are cumulative, meaning that any variations in estimated SOC will accumulate from charge cycle to charge cycle.

The present invention's method for computing a SOC with a higher accuracy than believed possible in the prior art includes establishing two thresholds that the SOC is updated within. These two thresholds are set by messages communicated by a battery maintenance and testing system to the smart battery 22 via the communication interface 144. The first threshold is set in response to an End of Discharge detected by the smart battery 22 when the battery maintenance and testing system detects a minimum voltage associated with the battery chemistry. After detecting the End of Discharge, the smart battery 22 resets the SOC to a minimum charge value. In an actual embodiment, the minimum charge value is zero. The smart battery 22 also sets the FCC value to the full charge capacity of that individual battery determined through actual experience with that battery by adjusting the FCC by adding to it whatever residual amount that remained in the SOC at the time the End of Discharge message was received by the smart battery 22 from the battery maintenance and testing system.

The second threshold is set in response to an End of Charge message sent by the battery maintenance and testing system to the smart battery 22. The battery maintenance and testing system employs charge algorithms that monitor the charge waveforms of the batteries as they are being charged. Based on this monitoring, the battery maintenance and testing system sends an End of Charge message when it determines that a battery is fully charged. Many suitable charge algorithms are well known in the art and may be used for this purpose. In response to the End of Charge message, the smart battery 22 immediately resets its SOC to the dynamically adjusted full charge capacity (FCC) value (discussed above) that is stored in the smart battery's non-volatile memory 142 and then stops counting charge current supplied to the smart battery 22. In this way, the smart battery has the ability to dynamically re-calibrate its SOC register at either end of the charge/discharge cycle using information maintained by the smart battery regarding the actual state of charge of that individual battery instead of the "one size fits all" approach taken in the prior art.

Another of the factors that affect the accuracy of the SOC is self discharge experienced by the smart battery 22 as a result of its own internal resistance. As this discharge is internal to the cells, it is impossible for the smart battery 22 to measure and therefore must be estimated. Statistical testing can be used to establish the expected self discharge rate for a specific manufacturer's cell and these values can be incorporated into an algorithm. Unfortunately the self discharge rate is temperature dependent, so the temperature of the cell must be measured to adjust the self discharge rate to compensate for temperature. What can't be estimated is the changes in self discharge that occur as a cell ages or begins to fail. An unexpected increase in self discharge would cause the SOC to become inaccurate—possibly indicating more capacity than actually exists in the smart battery 22. To mitigate the effect of a changing self discharge rate on the accuracy of the SOC, the present invention disables the SOC display by recording a critical error in the smart battery's non-volatile memory 142 after a predefined number of cycles (precluding the possibility of old age). The present invention also mitigates the effect of self discharge on the SOC by monitoring the amount of discrepancy attributed to self discharge and disabling the SOC display by recording a critical error in the smart battery's non-volatile memory 142 once the self discharge exceeds a predefined self discharge threshold. This second method is performed every time the battery is discharged in accordance with the method discussed below with reference to FIG. 7C. As is discussed in more detail below, if the residual value in the SOC is a positive number when the End of Discharge message is received by the smart battery from the battery maintenance and testing system, it means that there is unaccounted self discharge occurring. If this value exceeds a predefined self discharge threshold (that allows for minor variations in the charge cycling) the battery will log a critical error effectively ending its life.

Figure 7B:
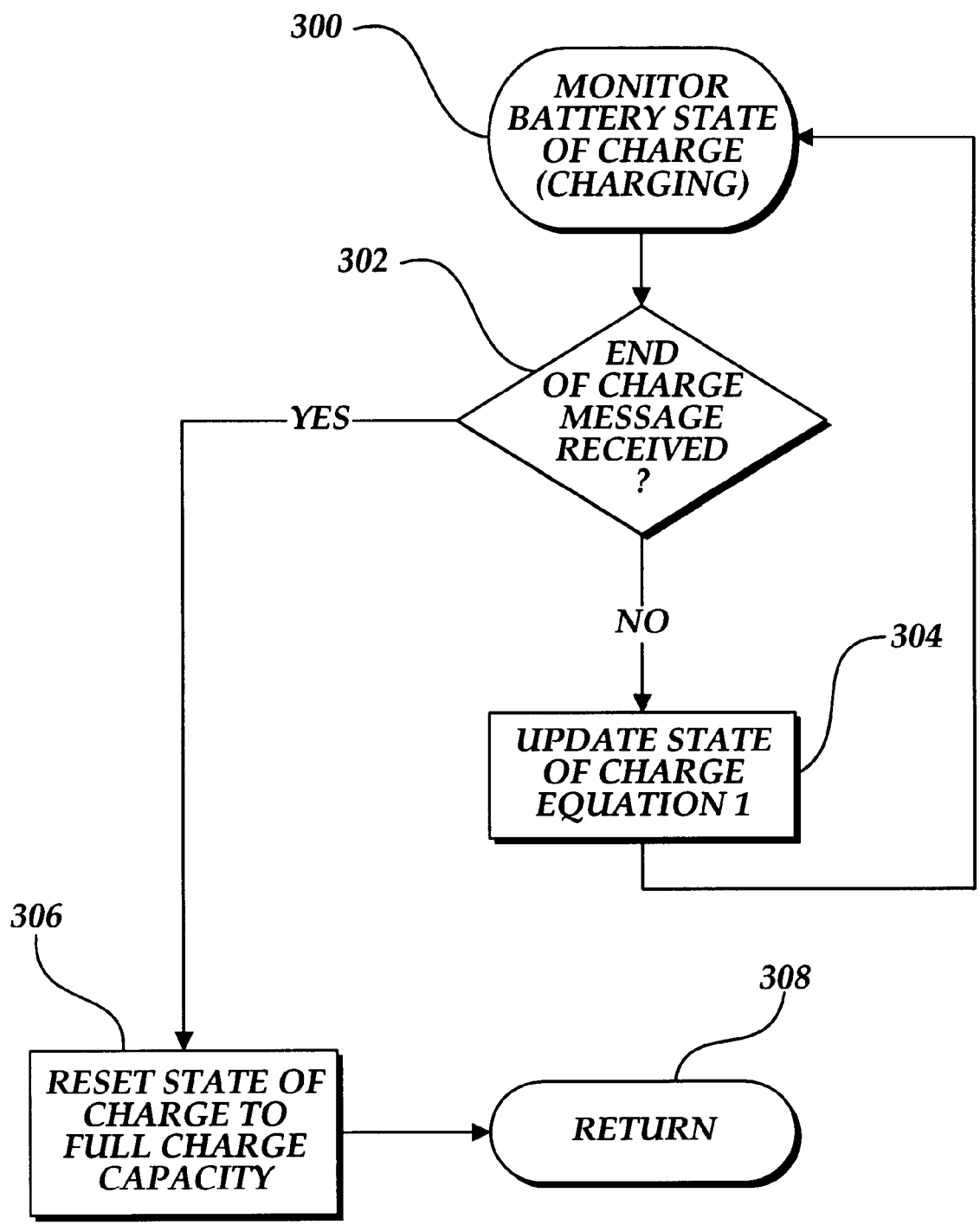
FIG. 7B is a flow chart illustrating the logic used by the battery of the present invention to monitor its state of charge during charging.
Figure 7C:
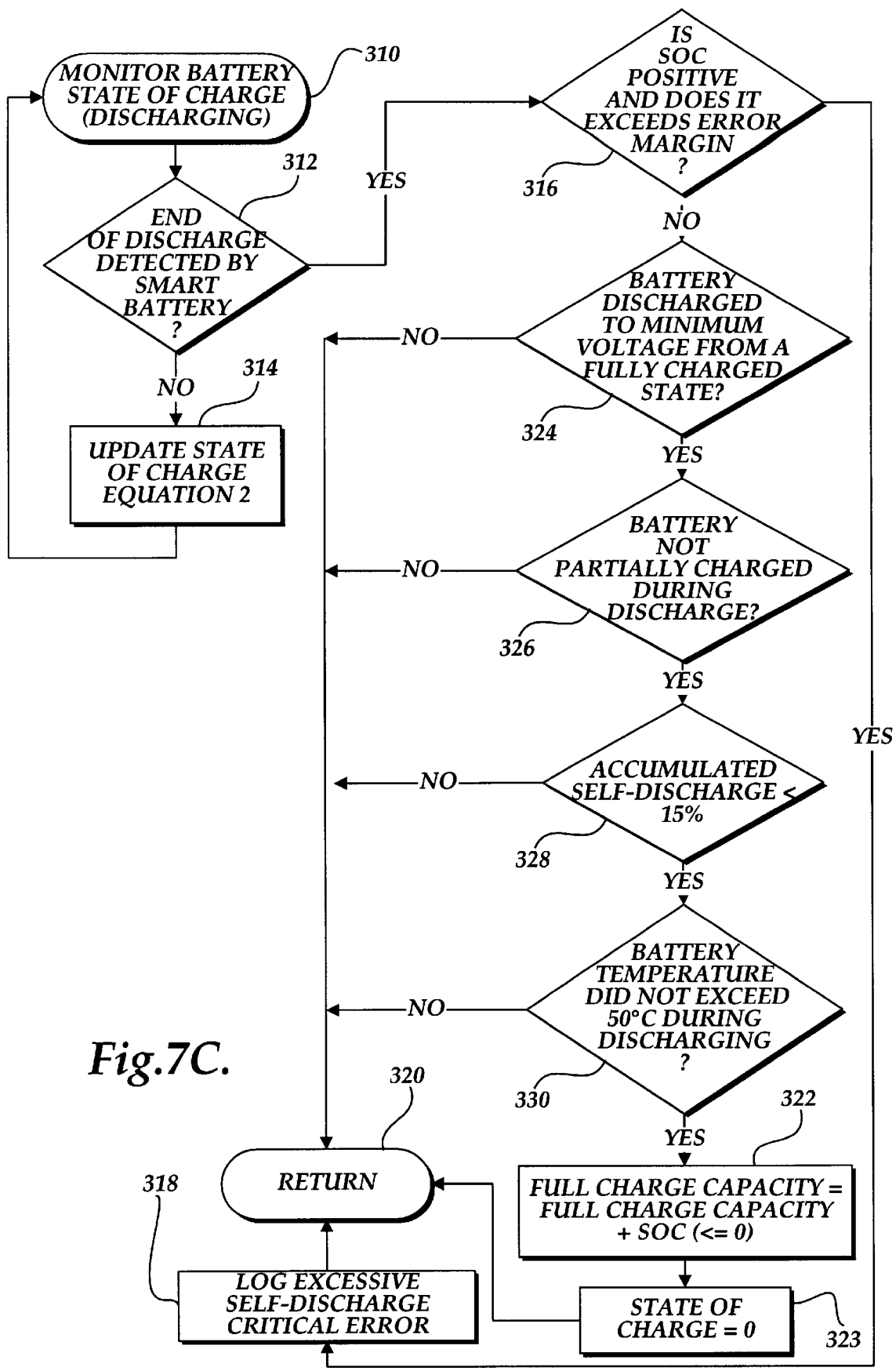
FIG. 7C is a flow chart illustrating the logic used by the battery of the present invention to monitor its state of charge during discharge.

The smart battery 22 continuously monitors its ability to reliably deliver charge as is illustrated in FIG. 7A The SOC of the battery is updated in a block 148 according to the methods illustrated in FIGS. 7B and 7C. When the smart battery 22 is being charged in a battery maintenance and testing system the state of charge is adjusted according to the method shown in FIG. 7B, which is entered at a block 300.

In a decision block 302, the smart battery 22 checks to see if an End of Charge message has been received on the communication interface 144. This message is sent by the battery maintenance and testing system when the charging algorithms of the battery maintenance and charging system detects that the battery has received its full state of charge. Until this message is received, the smart battery 22 updates its state of charge in a block 304 using equation (1):

Equation 1: Charging SOC equation $$SOC_1 = SOC_0 + \left[\frac{E_C \cdot (I_{C1} + I_{C0} - I_{B1} - I_{B0}) \cdot (t_1 - t_0)}{7200 \cdot C_{nom}}\right]_{SOC_0 < FCC}$$

In this equation:
- $SOC_1$ is the present value of the calculated SOC in percent. This value is calculated.
- $SOC_0$ is the prior value of the calculated SOC in percent. This value is calculated.
- $E_C$ is the efficiency of charge acceptance in percent. This value is a constant, based on temperature and current.
- $I_{C1}$ is the present charge current into the battery in amperes. This value is measured and is assumed to include the bias current $I_{B1}$.
- $I_{C0}$ is the prior charge current into the battery in amperes. This value is measured and is assumed to include the bias current $I_{B0}$.
- $I_{B1}$ is the present bias current for the electronics in the battery pack in amperes. This value is measured or estimated.
- $I_{B0}$ is the prior bias current for the electronics in the battery pack in amperes. This value is measured or estimated.
- $t_1$ is the present time of the measurements in seconds. This value is measured.
- $t_0$ is the prior time of the measurements in seconds. This value is measured.
- 7200 is a constant conversion factor accounting for averaging the currents, efficiency in percent, time in seconds, and capacity in amp hours.
- $C_{nom}$ is the battery manufacturer's capacity rating in amp hours. This value is a constant.
- FCC is the full charge capacity.

Equation 1 is essentially integrating the net current flowing into the battery and adjusting this for the battery's ability to absorb charge. The smart battery 22 continues to monitor its state of charge during charging by returning to block 300. When the battery maintenance and testing system detects that the smart battery 22 is no longer accepting charge, the battery maintenance and testing system sends an End of Charge message, which the smart battery 22 recognizes in decision block 302. The smart battery 22 responds by resetting its state of charge to the full charge capacity (FCC) value which is stored in the nonvolatile memory. In this way, the state of charge never exceeds the theoretical full charge capacity value. Control returns in a block 308 to the main processing loop after the End of Charge message is received from the battery maintenance and testing system. If the battery is removed from the battery maintenance and testing system before it has been fully charged or the smart battery 22 was charged in a charging unit that does not support the End of Charge message, the SOC calculated with Equation I is maintained by the smart battery 22 without the benefit of being calibrated to the FCC value until the next time the smart battery 22 is fully charged in the battery maintenance and testing system.

The method in FIG. 7C is executed beginning in block 310 when the smart battery is being discharged. While the smart battery 22 is waiting to detect an End of Discharge in a decision block 312, the smart battery updates the state of charge in a block 314 using equation (2):

Equation 2: Discharging SOC Equation $$SOC_1 = SOC_0 - \left\{ K_T \cdot E_D \cdot \left( \frac{I_{D1} + I_{D0} + I_{B1} + I_{B0}}{2} \right) \cdot \left( \frac{t_1 - t_0}{3600 \cdot C_{nom}} \right) \right\}$$

In this equation:

$SOC_1$ is the present value of the calculated SOC in percent. This value is calculated.

$SOC_0$ is the prior value of the calculated SOC in percent. This value is calculated.

$K_T$ is the temperature coefficient of discharge current and has no units. This value is calculated and is equal to 1 in one embodiment.

$I_{D1}$ is the present charge current into the battery in amperes. This value is measured and is assumed to exclude the bias current $I_{B1}$.

$I_{D0}$ is the prior charge current into the battery in amperes. This value is measured and is assumed to exclude the bias current $I_{B0}$.

$I_{B1}$ is the present bias current for the electronics in the battery pack in amperes. This value is measured or estimated.

$I_{B0}$ is the prior bias current for the electronics in the battery pack in amperes. This value is measured or estimated.

$E_D$ is the efficiency of discharge in percent.

$t_1$ is the present time of the measurements in seconds. This value is measured.

$t_0$ is the prior time of the measurements in seconds. This value is measured.

2 is a constant conversion factor accounting for averaging the currents.

3600 is a constant conversion factor accounting for time in seconds and capacity in amp hours.

$C_{nom}$ is the battery manufacturer's capacity rating in AH. This value is a constant.

For a smart battery 22 of the NiCd type, the smart battery 22 continues monitoring its state of charge by returning to the block 310 until it determines that it has reached an End of Discharge in block 312. In an actual embodiment of the invention, the smart battery determines that it has reached its End of Discharge when it has reached a terminal voltage of 10 volts. After the End of Discharge is detected in block 312, the smart battery 22 checks to see if the state of charge (SOC) that it has calculated is positive and if it exceeds a predefined error margin value in decision block 316. If the state of charge is positive, this indicates that there is a higher level of self discharge than is expected, thus indicating that the battery has reached the end of its useful life. In this case, the smart battery 22 logs an excessive self discharge critical error in a block 318 and then returns control the main processing loop (FIG. 7A) in a block 320. If, however, the state of charge either equals zero or is negative as detected in decision block 316, then the full charge capacity value FCC maintained in non-volatile memory is adjusted by adding the state of charge value (which is zero or a negative value) to its current value in a block 322. This has the effect of adjusting the full charge capacity FCC to reflect the actual capacity of the battery based on actual experience with the battery. Before the full charge capacity value FCC is adjusted, however, four tests are administered to check that the value in the SOC is probably not in error. The four tests that must first be passed are: (1) has the battery discharged to a minimum voltage from a fully charged state in a block 324; (2) has the battery not been partially charged during the discharge in a block 326; (3) is the accumulated self discharge less than 15% of the full charge capacity in a block 328; and (4) has the battery temperature not exceeded 50° C. during discharge in a decision block 330. If the answer to any of these four tests 324, 326, 328 and 330 is no, then control is returned to the main processing loop in the block 320. Otherwise, the full charge capacity in nonvolatile memory is reset to its former value plus the state of charge value SOC in block 322 (which is 0 or a negative value), and then the state of charge value maintained by the smart battery 22 is set to zero (indicating the battery has been fully discharged).

For a smart battery 22 based on the SLA chemistry, the end of discharge is reached when the smart battery 22 reaches a State of Charge of approximately 25% of its full charge capacity when it has an internal impedance of about 0.128 Ohms. This value has been derived empirically. This internal impedance, under a normal operating load of 1 amp, corresponds to a terminal voltage of 11.7 volts. This terminal voltage is used for the nominal low battery threshold. If however the current varies from 1 Amp the following formula is used: V(threshold)=11.7−((I(measured)−I(nom)) *0.128) where I(nom) in this case is 1 Amp.

Figure 8:
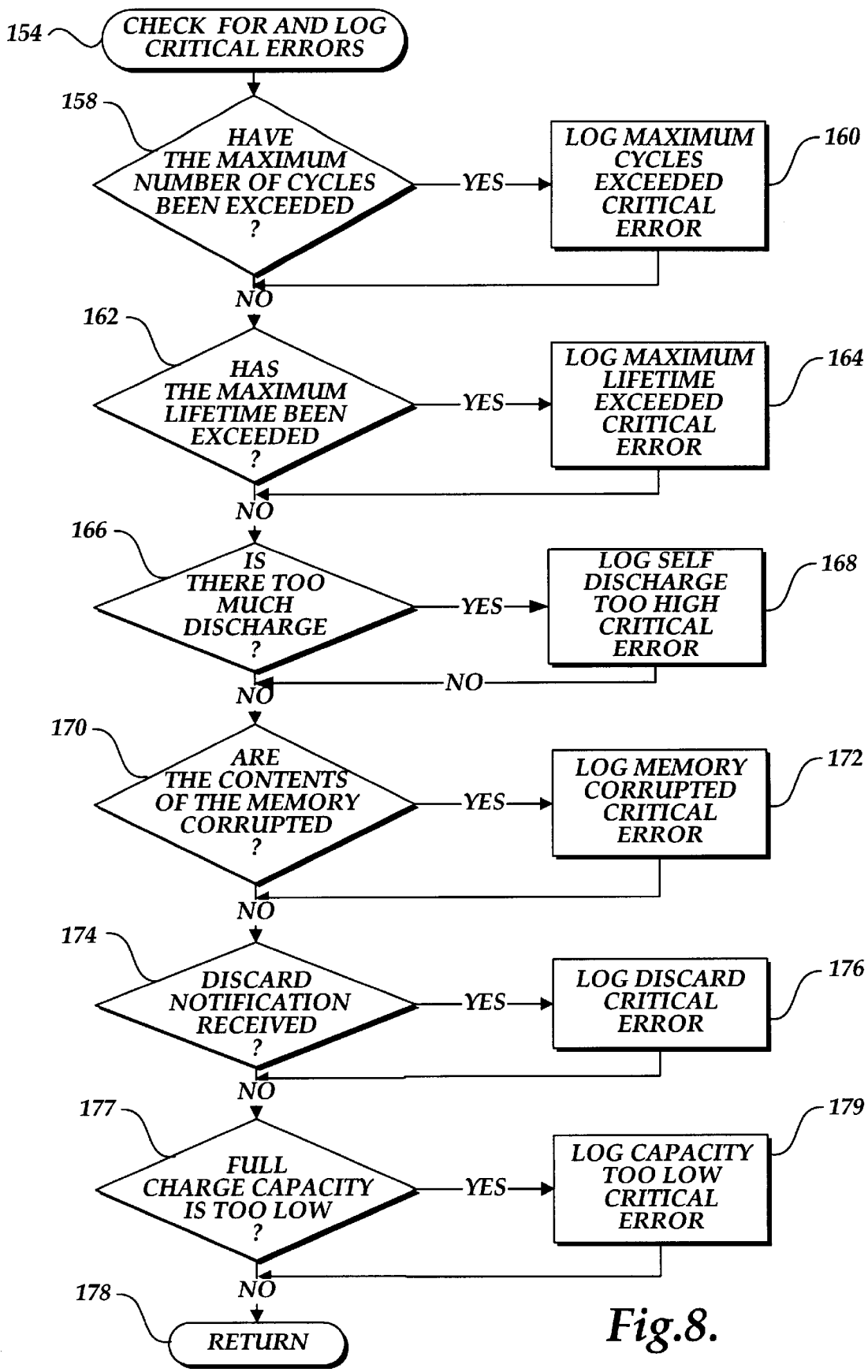
FIG. 8 is a flow chart illustrating the logic used by the battery of the present invention to monitor and test for battery discard.

The routine for checking for and logging critical errors 154, i.e., errors indicating that the smart battery should be discarded, is shown in FIG. 8. In a block 158, the battery 22 checks the total number of cycles that it has been through against a maximum number of cycles that the battery can theoretically withstand. For example, if the battery 22 is a NiCd battery, in an actual embodiment of the invention, this maximum number is 750 cycles. The number of cycles used for the maximum number of cycles permitted may vary according to the actual battery cell used and may be determined, for example, from data provided by the manufacturer of the battery cell or by actual product testing of the battery cell. Therefore, if the total cycles experienced by the battery exceeds a maximum number, the battery logs in non-volatile memory 142 a maximum cycles critical error and date stamp in a block 160. The battery then checks in a block 162 if a maximum lifetime of the battery has been exceeded. In one embodiment of the invention, the maximum lifetime of a battery is set at three years. If this maximum lifetime has been exceeded, then a maximum lifetime exceeded critical error is logged in the non-volatile memory 142 in a block 164.

The battery 22 is also continuously monitoring its self-discharge, as is discussed above. Therefore, in a decision block 166, if this self-discharge exceeds a predetermined limit, an excessive self-discharge critical error is logged in the non-volatile memory 142 in a block 168. The self discharge rate is time and temperature dependent. For example, to account for self-discharge, the SOC is adjusted for a NiCd smart battery 22 according to the following formulas: when the temperature of the smart battery 22 is less than 30 C and the time since the last End of Charge message is less than 24 hours, the formula used is: $SOC_1 = SOC_0 - ((SOC_0 * 0.15)/24)$. If the time is greater than 24 hours since the End of Charge message is sent, then $SOC_1 = SOC_0 -$ $((SOC_0*0.03)/24)$. For temperatures more than 30 C, if the time since last End of Charge is greater than 24 hours then $SOC_1=SOC_0-((SOC_0*0.22)/24)$. If the time is greater than 24 hours then $SOC_1=SOC_0-((SOC_0*0.05)/24)$.

The battery 22 may also periodically perform a CRC check of the contents of the non-volatile memory 142 and verifies the value computed by this CRC check against a known value to determine if the program contents stored in the non-volatile memory have been corrupted in a decision block 170. If these contents are found to be corrupted, a memory corrupted critical error is logged in the non-volatile memory in a block 172. It is also possible that a host defibrillator, battery maintenance and testing system, or other device with which the battery is communicating has detected a critical error in the battery 22. Consequently, in a decision block 174, the logic determines if a discard notification has been received from such a device. If so, the battery 22 logs a corresponding critical error in the non-volatile memory in a block 176. The battery also periodically checks the full charge capacity in a decision block 177 and logs a capacity too low critical error in a block 179 if the full charge capacity is below a predefined limit. In an actual embodiment of the invention, the predefined limit is set to 80% of the nominal Full Charge Capacity. Processing then returns to the main processing routine 146 (FIG. 7A) in a block 178.

Figure 9:
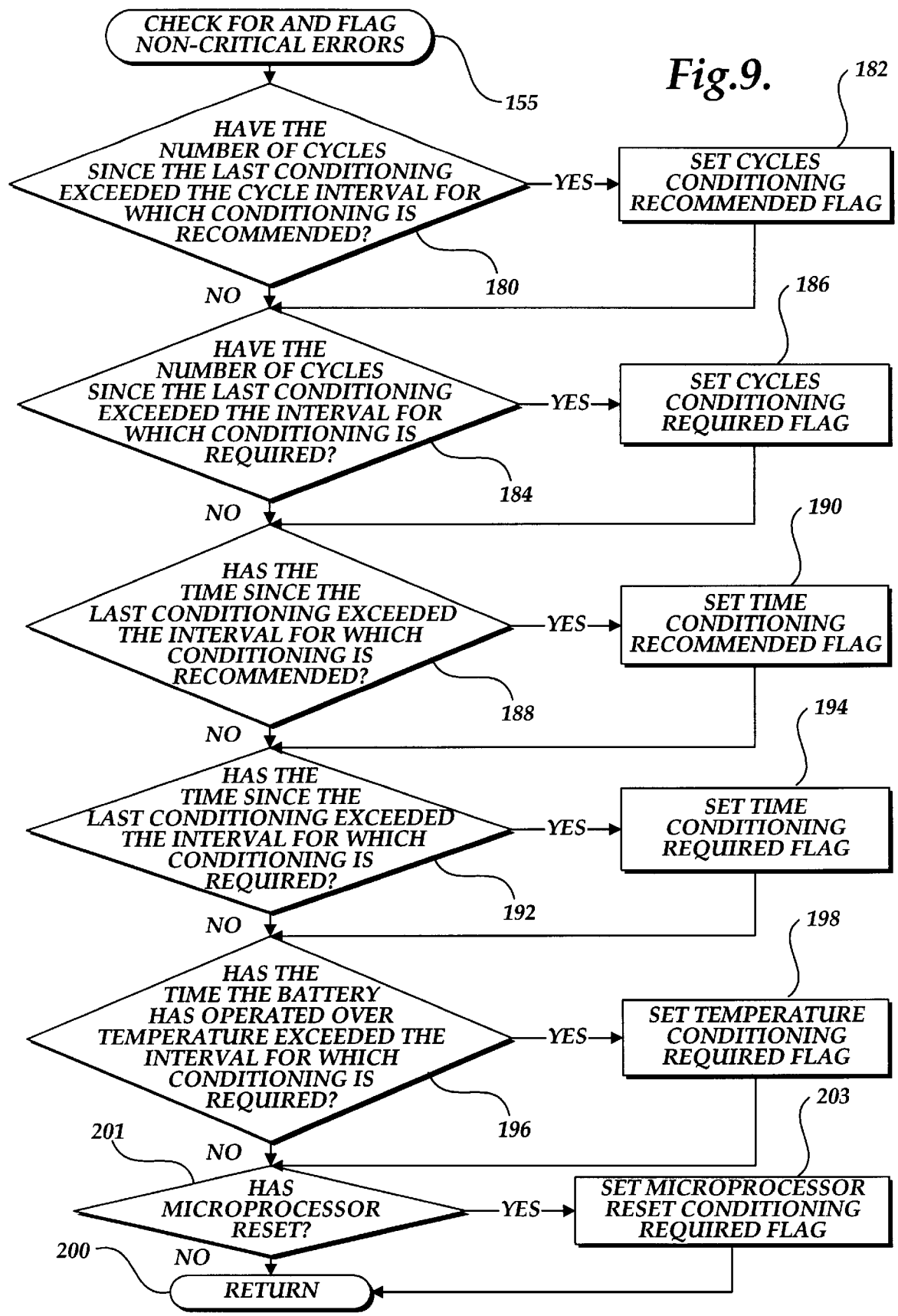
FIG. 9 is a flow chart illustrating the logic used by the battery of the present invention to monitor and test for battery maintenance.

The routine for checking and flagging non-critical errors 155, i.e., errors indicating that the smart battery 22 requires maintenance, is shown in FIG. 9. In a decision block 180 the smart battery 22 checks if the number of cycles since the last conditioning of the smart battery 22 has exceeded a predefined number of cycles for which conditioning is recommended. The predefined number of cycles is 90 cycles in one embodiment of the present invention. If the cycles counted by the smart battery 22 since the last conditioning have exceeded this predefined number of cycles value, then a cycles conditioning recommended flag is set in the non-volatile memory 142 in a block 182. The number of cycles since last conditioning is then compared against a predefined number of cycles after which conditioning is required in a decision block 184. In one embodiment of the present invention this predefined number of cycles value is 180 cycles. If this predefined number of cycles value has been reached, a cycles conditioning required flag is set in the non-volatile memory 142 in a block 186.

In a decision block 188, the time since the last conditioning is compared against a predefined interval for which conditioning is recommended. This predefined interval is 90 days in one embodiment of the present invention. If the time since the last conditioning exceeds this predefined interval, then a time conditioning recommended flag is set in the non-volatile memory 142 in a block 190. In a decision block 192, the time since the last conditioning is then compared against a predefined interval for which conditioning is required. In one embodiment of the present invention, this predefined interval is 180 days. If the time since last conditioning recorded by the smart battery 22 exceeds this predefined interval, then a time conditioning required flag is set in the non-volatile memory 142 in a block 194.

The smart battery 22 checks to see if it has operated over temperature for a period that is longer than a predefined time over temperature value in a decision block 196. In one embodiment of the invention, this predefined time over temperature value is five hours operating in a temperature range that exceeds 50° C. If the time over temperature recorded by the smart battery has exceeded the predefined time over temperature value, a temperature conditioning required flag is set in a block 198. A microprocessor reset is detected in a decision block 201. If the microprocessor resets, a microprocessor reset flag is set in a block 203. All of these flags, or non-critical errors, are recorded in non-volatile memory 142 and then operation is returned to the main processing routine loop 146 (FIG. 7A) in a block 200. Those of ordinary skill in the art will appreciate that the time intervals and cycle thresholds referred to above may vary depending on battery chemistry and charging techniques.

Figure 10:
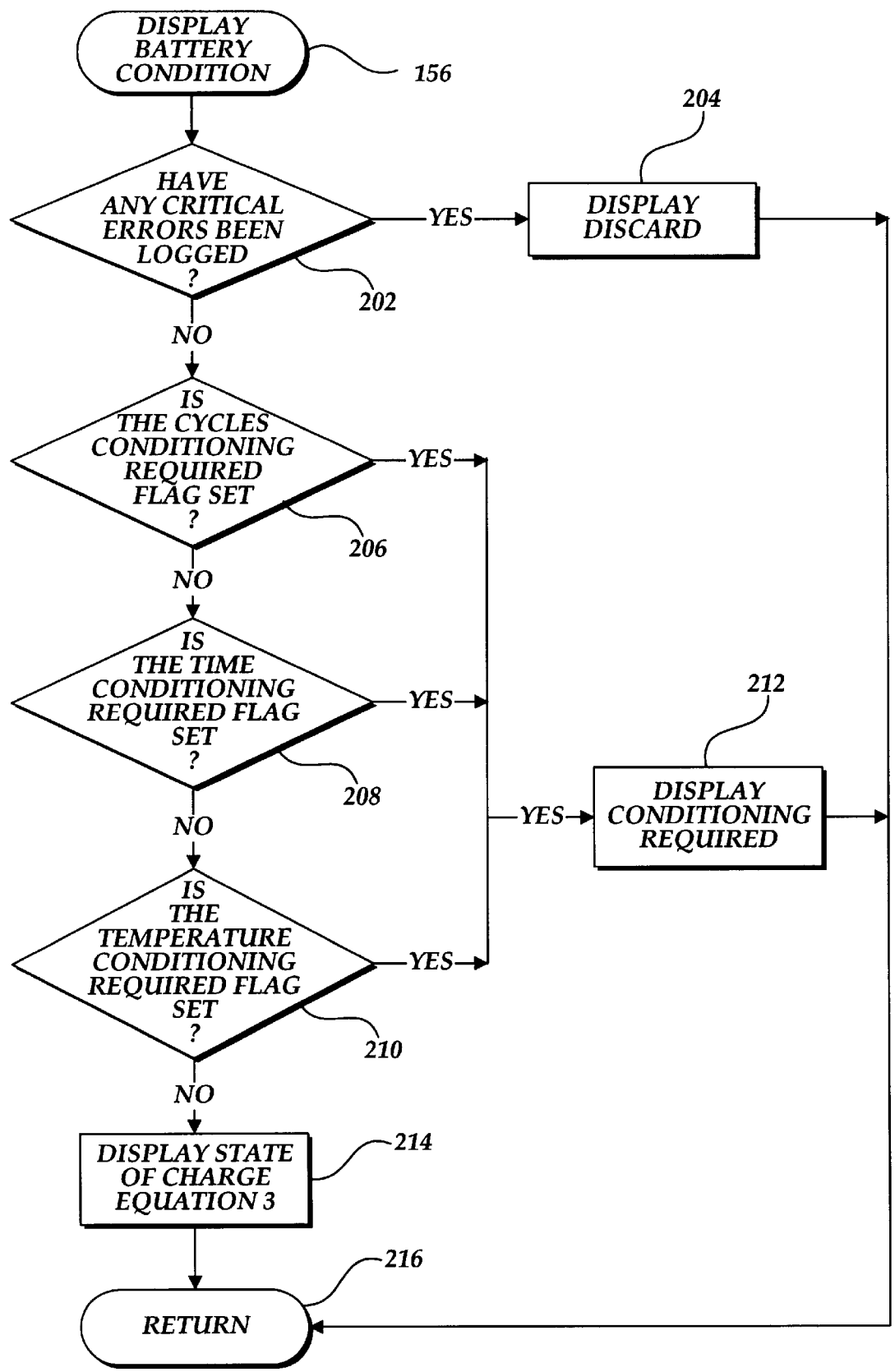
FIG. 10 is a flow chart illustrating the logic used by the battery of the present invention to display the battery's condition to a user.

FIG. 10 illustrates the routine used by the battery 22 to display its condition to a user who has requested the same by pushing the depressible keypad 34 of the user interface and display area 32. The battery first determines in a block 202 if any critical errors have been logged in its non-volatile memory 142. If any such error has been logged, the lighted display 76 indicates that the battery is "dead" or needs to be discarded by lighting the LED's 76a–d in a discard pattern in a block 204. In an actual embodiment of the present invention, a discard condition is indicated by not lighting any LED's in response to the user's request.

Returning to decision block 202, if no critical errors are found in non-volatile memory 142, then the battery 22 checks in a decision block 206 if the cycle conditioning required flag has been set. If so, the battery 22 lights the LED's 76a–d of the lighted display 76 in a conditioning required pattern in a block 212. Otherwise, in a decision block 208 it is determined if the time conditioning required flag has been set. If so, the battery lights the LED's 76a–d in a conditioning required pattern in block 212. Otherwise, in a decision block 210 it is determined if the temperature conditioning required flag has been set and if so the conditioning required pattern is lighted in block 212. In other words, if any of the above-identified flags have been set, then the battery 22 displays the conditioning required pattern in a block 212. The conditioning required display pattern, in one embodiment the invention, alternates flashing the first and third LED's with the second and forth LED's.

It should be noted that the flags checked in blocks 206, 208 and 210 are stored in the nonvolatile memory 142 of the battery 22 and the order in which they are checked is unimportant. If the smart battery 22 does not find a critical error in a block 202 or a non-critical error in a blocks 206, 208, or 210, then it displays in a block 214 the state of the charge of the battery and then returns in a block 216 to the main processing routine shown in FIG. 7A.

In one embodiment of the invention a relative state of charge that includes a "reserve factor" is displayed using the LED's 76a–d. One LED flashes if the relative state of charge is less than or equal to 0%; one LED lights steadily if the relative state of charge is greater than 0% but less than or equal to 25%; two LED's light steadily if the relative state of charge is greater than 25% but less than or equal to 50%; three LED's light steadily if the relative state of charge is greater than 50% but less than or equal to 75%; and, four LED's light steadily if the relative state of charge is greater than 75%.

In computing the relative SOC for the display, a reserve factor, or error margin, is used when computing the reserve capacity that the LED's will indicate according to the equation:

Equation 3: Display SOC equation $$DisplaySOC = \frac{(SOC_1 - R) \cdot 100}{100 - R}$$

In this equation:

Display SOC is the value of SOC to display in percent. This value is calculated.

$SOC_1$ is the present value of the calculated SOC in percent. This value is calculated.

R is the value of the reserve capacity in percent. This value is a constant and in one embodiment of the invention is 15 (representing 15%).

As noted above, in addition to reporting the battery's condition to the user through the lighted display 76, the smart battery 22 communicates with other devices. The messages relating to the dynamic state of charge calculations/adjustments are discussed above. External devices may access the smart battery to retrieve information that it maintains about itself For instance, the smart battery 22 can report its state of charge, request maintenance, or indicate that it has reached the end of its useful life and should be discarded.

Figure 11:
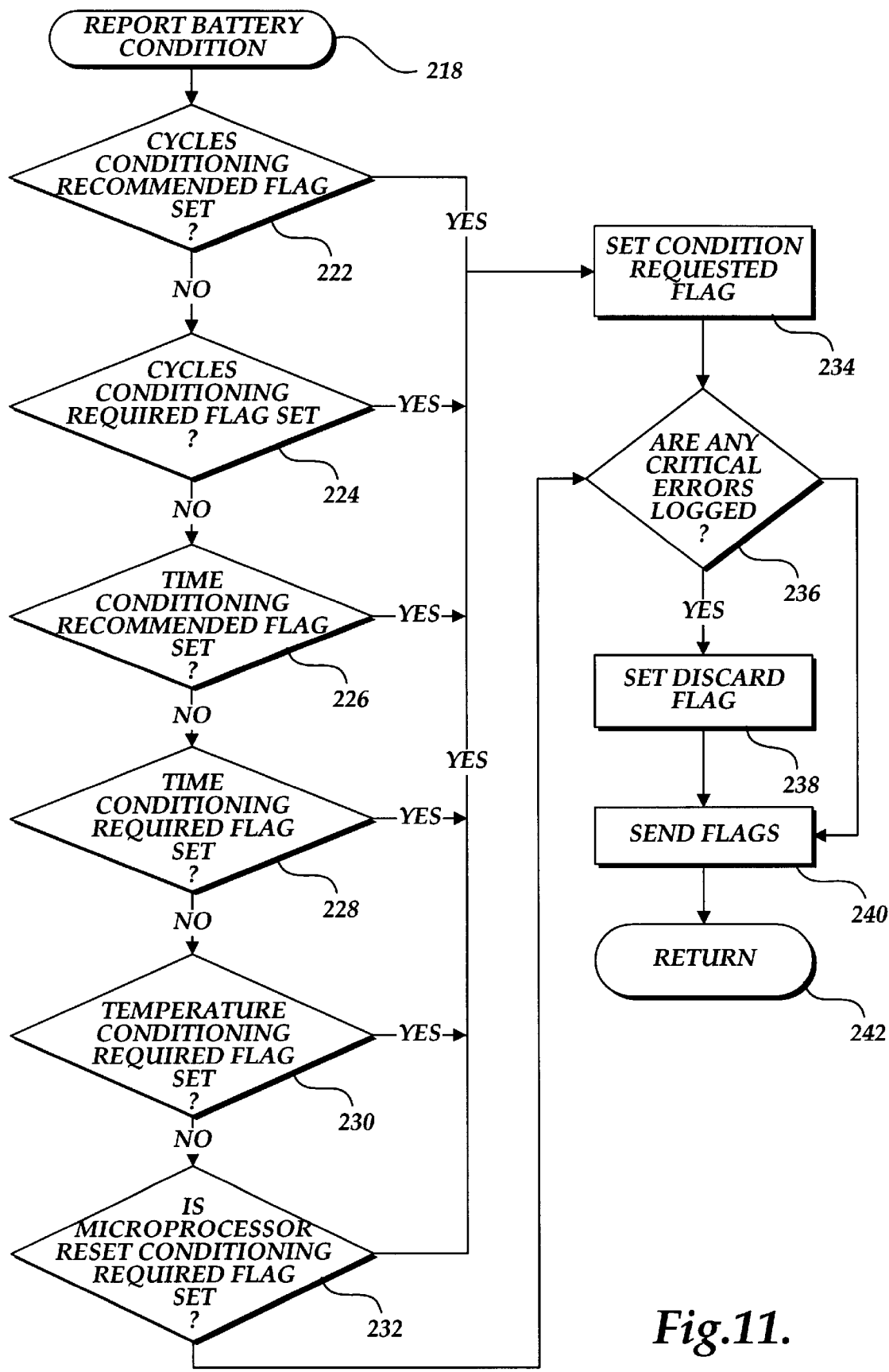
FIG. 11 is a flow chart illustrating the logic used by the battery of the present invention to report the battery's condition to another device.

The smart battery 22 reports its status through the communication interface 142 according to the routine shown in FIG. 11. In a decision block 222, the battery 22 checks whether the cycles conditioning recommended flag 182 is set; in a decision block 224 the battery 22 determines whether the cycles conditioning required flag 194 is set; in a decision block 226 the battery determines whether the time conditioning recommended flag 190 is set; in a block 228 the battery determines whether the time conditioning required flag 194 is set; in a block 230 the battery determines whether the temperature conditioning required flag 198 is set; and, in a block 232 the battery determines whether the microprocessor reset flag has been set. If any of the flags checked in a blocks 222, 224, 226, 228, 230, or 232 are set, a conditioning requested flag is set in a block 234.

The smart battery 22 then checks to see if any critical errors have been logged in the nonvolatile memory in a block 236. If a critical error has been found, then a discard flag is set in a block 238. The flags set in blocks 234 and 238 are then communicated via the communication interface 144 to the host devices in a block 240 in accordance with the SMBus standard. It will be recognized by those of ordinary skill in the art that the device receiving these flags will process them as necessary in order to condition, charge or otherwise test the battery 22. Control is then returned in a block 242 to the main processing routine of FIG. 7A.

Figure 12:
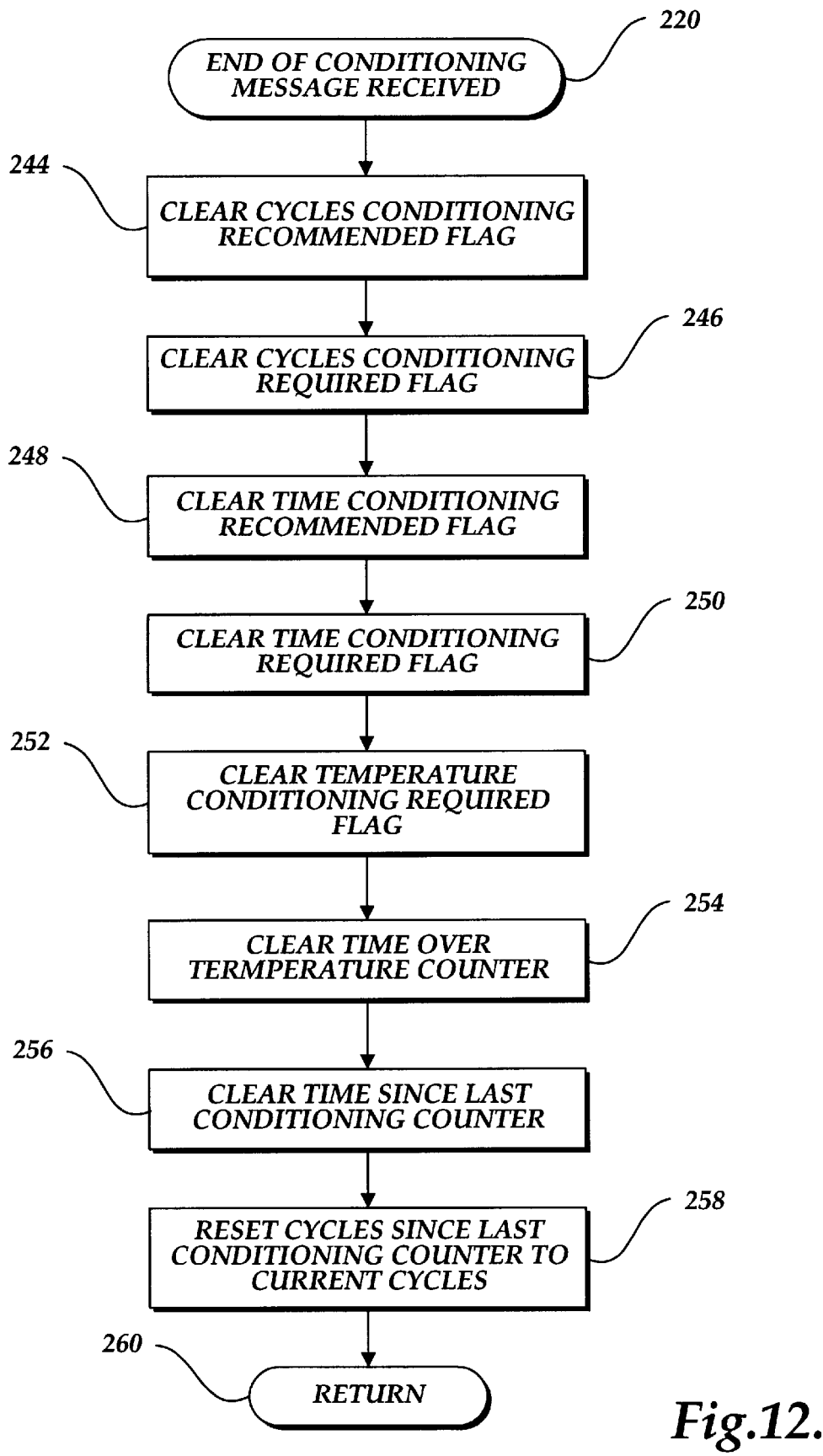
FIG. 12 is a flow chart illustrating the logic used by the battery of the present invention after the battery has been notified that the battery has been successfully conditioned.

In addition to sending information about its condition to external devices, the battery 22 can receive and process notifications from other devices via the communication interface pads 56 and communication interface 144. The notifications used in the SOC process are described above. Following conditioning, a battery maintenance and testing system can notify the smart battery 22 after the smart battery has been conditioned. The routine implemented by the battery 22 when an End of Conditioning notification is received is illustrated in FIG. 12. Essentially, this routine resets all the non-critical error flags. In a block 244, the cycles conditioning recommended flag 182 is cleared; in a block 246 the cycles conditioning required flag 186 is cleared; in a block 248 the time conditioning recommended flag 190 is cleared; in a block 250 the time conditioning required flag 194 is cleared; and, in a block 252 the temperature conditioning required flag 198 is cleared. In addition, the time since the last conditioning counter is cleared in a block 256 and the cycle since last conditioning counter is set to the current number of cycles the battery has been through in a block 258. Control is then returned in a block 260 to the main processing routine of FIG. 7A.

While the preferred embodiment of the invention has been illustrated and described, it will be appreciated that various changes can be made therein without departing from the spirit and scope of the invention. Accordingly, it is not intended that the scope of the invention be limited by the actual embodiments describe above. Instead, the invention should be determined entirely by reference to the claims that follow.

What is claimed is:

1. A method for self monitoring a rechargeable battery's ability to reliably deliver charge to a host device, the method comprising:

dynamically calculating a state of charge (SOC) that quantifies the ability of the rechargeable battery to deliver charge to a host device as charge is drawn from and supplied to the battery;

charging the rechargeable battery until an end of charge message is received, the end of charge message indicating that the rechargeable battery has stopped accepting charge; and adjusting the SOC to a full charge capacity value if the SOC exceeds the full charge capacity value when the end of charge message is received by the rechargeable battery.

2. The method of claim 1, further comprising:

discharging the rechargeable battery until an end of discharge message is received, the end of discharge message indicating that the rechargeable battery has reached a nominal low battery threshold;

adjusting the full charge capacity by adding the SOC to the full charge capacity if the SOC is less than or equal to zero when the end of discharge message is received by the rechargeable battery; and resetting the SOC to a minimum charge value after dynamically adjusting the full charge capacity.

3. The method of claim 2, further comprising not dynamically adjusting the full charge capacity by adding the SOC to the full charge capacity when the end of discharge message is received if any of the following conditions is not met during a discharge cycle: (i) the rechargeable battery was discharged from a fully charged state; (ii) the rechargeable battery was not partially charged; (iii) an accumulated self-discharge value does not exceed a predefined percentage of an estimated initial full charge capacity; and (iv) the rechargeable battery temperature did not exceed a predefined temperature limit.

4. The method of claim 2, further comprising:

setting a discard flag when the end of discharge message is received and the SOC is positive and exceeds a predefined error margin.

5. The method of claim 4, further comprising adjusting the SOC with an efficiency coefficient.

6. The method of claim 5, further comprising adjusting the efficiency coefficient as the SOC changes.

7. The method of claim 6, further comprising adjusting the SOC with a self discharge rate.

8. The method of claim 7, further comprising adjusting the self discharge rate to reflect for the time since the rechargeable battery was last charged.

9. The method of claim 1, wherein the SOC is dynamically calculated by a monitoring circuit using a discharging SOC equation.

10. The method of claim 9, wherein the discharging SOC equation is:

$$SOC_1 = SOC_0 - \left\{ K_T \cdot E_D \cdot \left( \frac{I_{D1} + I_{D0} + I_{B1} + I_{B0}}{2} \right) \cdot \left( \frac{t_1 - t_0}{3600 \cdot C_{nom}} \right) \right\}$$

the variable in the discharging SOC equation being defined as:

$SOC_1$ is a present value of the calculated SOC in percent;
$SOC_2$ is a prior value of the calculated SOC in percent;
$K_T$ is a temperature coefficient of discharge current and has no units;
$I_{D1}$ is a present charge current into the rechargeable battery in amperes;
$I_{D0}$ is a prior charge current into the rechargeable battery in amperes;
$I_{B1}$ is a present bias current for the monitoring circuit in the rechargeable battery in amperes;
$I_{B0}$ is a prior bias current for the monitoring circuit in the rechargeable battery in amperes;
$t_1$ is a present time of the measurements in seconds;
$t_0$ is a prior time of the measurements in seconds;
$E_D$ is the efficiency of discharge in percent;
2 is an averaging factor;
3600 is a constant conversion factor accounting for time in seconds and capacity in amp hours;
$C_{nom}$ is a battery manufacturer's capacity rating in AH; and
$SD_T$ is an amount of capacity lost due to self discharge in percent.

11. The method of claim 9, wherein the charging SOC equation is:

$$SOC_1 = SOC_0 + \left[ \frac{E_C \cdot (I_{C1} + I_{C0} - I_{B1} - I_{B0}) \cdot (t_1 - t_0)}{7200 \cdot C_{nom}} \right]\Big|_{SOC_0 < FCC}$$

the variables in the discharging SOC equation being defined as:

$SOC_1$ is a present value of the calculated SOC in percent;
$SOC_0$ is a prior value of the calculated SOC in percent;
$E_C$ is a efficiency of charge acceptance in percent;
$I_{C1}$ is a present charge current into the rechargeable battery in amperes;
$I_{C0}$ is a prior charge current into the battery in amperes;
$I_{B1}$ is a present bias current for the monitoring circuit in the rechargeable battery in amperes;
$I_{B0}$ is a prior bias current for the monitoring circuit in the rechargeable battery in amperes;
$t_1$ is a present time of the measurements in seconds;
$t_0$ is a prior time of the measurements in seconds;
7200 is a constant conversion factor accounting for averaging;
$C_{nom}$ is a battery manufacturer s capacity rating in amp hours; and
FCC is the full charge capacity.

12. The method of claim 1, further comprising maintaining a log of critical errors in the non-volatile memory, each critical error indicating that the rechargeable battery may not be reliable and should be discarded.

13. The method of claim 12, wherein a critical error is logged if the number of cycles that the rechargeable battery has been through exceeds a predefined maximum number of cycles.

14. The method of claim 12, wherein a critical error is logged if an interval of the time that the rechargeable battery has been in use exceeds a predefined maximum lifetime.

15. The method of claim 12, wherein a critical error is logged if the contents of a non-volatile memory of the rechargeable battery have become corrupted.

16. The method of claim 12, wherein a critical error is logged if the rechargeable battery receives a notification from another device that the rechargeable battery should be discarded.

17. The method of claim 12, wherein a critical error is logged if the full charge capacity is less than a predefined full charge capacity minimum value.

18. The method of claim 12, wherein an indication that the rechargeable battery may not be reliable and should be discarded is displayed if a critical error has been recorded in the log of critical errors.

19. The method of claim 12, wherein a critical error is communicated by the rechargeable battery to a host device via a communication interface.

20. The method of claim 12, further comprising displaying the ability of the rechargeable battery to reliably deliver charge to a host device by displaying an indication of the SOC of the rechargeable battery.

21. The method of claim 1, further comprising maintaining at least one non-critical critical error flag in a non-volatile memory of the rechargeable battery, each non-critical error flag indicating that the rechargeable battery requires maintenance.

22. The method of claim 21, a cycles conditioning recommended flag is set if a count of cycles experienced by the rechargeable battery exceeds a cycles conditioning recommended interval.

23. The method of claim 21, a cycles conditioning required flag is set if a count of cycles experienced by the rechargeable battery exceeds a cycles conditioning required interval.

24. The method of claim 21, a time conditioning recommended flag is set if a time interval since the rechargeable battery was last conditioned exceeds a cycles conditioning recommended interval.

25. The method of claim 21, time conditioning required flag is set if a time interval since the rechargeable battery was last conditioned exceeds a time conditioning required interval.

26. The method of claim 21, an indication that the rechargeable battery requires maintenance is displayed if a non-critical error has occurred.

27. The method of claim 26, wherein the indication that the rechargeable battery requires maintenance is only displayed when the non-critical error is of a predefined type that indicates that maintenance is required.

28. The method of claim 27, wherein the predefined type is a cycles conditioning required flag that is set if a count of cycles experienced by the rechargeable battery exceeds a predefined cycles conditioning required interval.

29. The method of claim 27, wherein the predefined type includes a time conditioning required flag that is set if a time interval experienced by the rechargeable battery exceeds a predefined time conditioning required interval.

30. The method of claim 27, wherein the predefined type includes a temperature conditioning required flag that is set if a cumulative time over temperature interval experienced by the rechargeable battery exceeds a predefined temperature conditioning required interval.

31. The method of claim 26, wherein the non-critical error is communicated to a host device via a communication interface as a request for maintenance.

32. A smart battery apparatus, comprising:

a smart battery housing;

a user interface display area mounted upon the smart battery housing;

a monitoring circuit mounted upon a circuit board for monitoring a state of charge (SOC) of the smart battery and displaying the SOC on the user interface display area; and a plurality of electrically conductive rods coupled to the circuit board in a manner that conducts an electrical signal through the electrically conductive rods to the monitoring circuit.

33. The apparatus of claim 32, wherein the monitoring circuit has a central processing unit that is programmed to adjust the SOC to a full charge capacity (FCC) when a host device communicates to the monitoring circuit that the host device has detected that the smart battery has stopped accepting charge.

34. The apparatus of claim 33, wherein the central processing unit is programmed to adjust the FCC if the SOC is less than or equal to zero when the host device communicates to the monitoring circuit that the host device has detected that the smart battery has been fully discharged.

35. The apparatus of claim 32, wherein the monitoring circuit has a central processing unit that monitors the smart battery's need for maintenance.

36. The apparatus of claim 35, wherein the monitoring circuit is coupled to a non-volatile memory circuit and the central processing unit indicates that the battery requires maintenance by setting in the non-volatile memory a cycles conditioning required flag in if a count of cycles experienced by the rechargeable battery exceeds a predefined cycles conditioning required interval.

37. The apparatus of claim 35, wherein the monitoring circuit is coupled to a non-volatile memory circuit and the central processing unit indicates that the battery requires maintenance by setting in the non-volatile memory a time conditioning required flag that is set if a time interval experienced by the rechargeable battery exceeds a predefined time conditioning required interval.

38. The apparatus of claim 35 wherein the monitoring circuit is coupled to a non-volatile memory circuit and the central processing unit indicates that the battery requires maintenance by setting in the non-volatile memory a temperature conditioning required flag that is set if a cumulative time over temperature interval experienced by the rechargeable battery exceeds a predefined temperature conditioning required interval.

39. The apparatus of claim 35, wherein the central processing unit communicates the need for maintenance to a host device via a communication interface that is coupled to the central processing unit.

40. The apparatus of claim 35, wherein the central processing unit determines when the smart battery should be discarded by logging a critical error in a non-volatile memory that is coupled to the central processing unit.

41. The method of claim 40, wherein a critical error is logged by the central processing unit if a count maintained by the central processing unit of the number of cycles that the rechargeable battery has been through exceeds a predefined maximum number of cycles.

42. The method of claim 40, wherein a critical error is logged by the central processing unit if an interval maintained by the central processing unit of the time that the rechargeable battery has been in use exceeds a predefined maximum lifetime.

43. The method of claim 40, wherein a critical error is logged by the central processing unit if a program content of the non-volatile memory has become corrupted.

44. The method of claim 40, wherein a critical error is logged by the central processing unit if the rechargeable battery receives a notification from a host device that the smart battery should be discarded.

45. The method of claim 40, wherein a critical error is logged by the central processing unit if a full charge capacity is less than a predefined full charge capacity minimum value.

46. The method of claim 40, wherein the central processing unit displays through the user interface and display an indication of that the rechargeable battery may not be reliable and should be discarded if the central processing unit has logged a critical error.

47. The apparatus of claim 40, wherein a critical error is communicated by the smart battery to a host device via a communication interface.

* * * * *

UNITED STATES PATENT AND TRADEMARK OFFICE
CERTIFICATE OF CORRECTION

PATENT NO.   : 6,198,253 B1
DATED        : March 6, 2001
INVENTOR(S)  : W.D. Kurle et al.

It is certified that error appears in the above-identified patent and that said Letters Patent is hereby corrected as shown below:

Title page 1,
Item [56], References Cited, OTHER PUBLICATIONS, "Revision 1.0, Feb. 15, 1995." should read -- *Revision 1.0, Feb. 15, 1995.* --
Item [57], ABSTRACT, "another devices" should read -- other devices --

Title page 2,
Item [56], References Cited OTHER PUBLICATIONS, "Revision 1.0, Jun. 27, 1996." should read -- *Revision 1.0, Jun. 27, 1996.* --

Column 17,
Line 9, "$SOC_2$" should read -- $SOC_0$ --
Line 43, "a efficiency" should read -- an efficiency --
Line 56, "manufacturer s capacity" should read -- manufacturer's capacity --

Column 18,
Line 29, after "claim 21," insert -- wherein --
Line 33, after "claim 21," insert -- wherein --
Line 37, after "claim 21," insert -- wherein --
Line 41, after "claim 21," insert -- wherein --
Line 45, after "claim 21," insert -- wherein --

UNITED STATES PATENT AND TRADEMARK OFFICE
CERTIFICATE OF CORRECTION

PATENT NO. : 6,198,253 B1
DATED : March 6, 2001
INVENTOR(S) : W.D. Kurle et al.

It is certified that error appears in the above-identified patent and that said Letters Patent is hereby corrected as shown below:

Column 19,
Line 32, "flag in if" should read -- flag if --

Column 20,
Line 36, after "interface" delete "and display"
Line 37, after "indication" delete "of"

Signed and Sealed this

Fifth Day of February, 2002

Attest:

JAMES E. ROGAN
*Director of the United States Patent and Trademark Office*

*Attesting Officer*